(12) United States Patent
Thies et al.

(10) Patent No.: US 6,656,956 B2
(45) Date of Patent: Dec. 2, 2003

(54) BENZIMIDAZOLE DERIVATIVES, PROCESSES FOR PREPARING THEM AND THEIR USE AS PHARMACEUTICAL COMPOSITIONS

(75) Inventors: Claudia Thies, Biberach (DE); Christine Braun, Giubiasco (CH); Ralf Anderskewitz, Laupheim (DE); Horst Dollinger, Schemmerhofen (DE); Pascale Pouzet, Biberach (DE); Herbert Nar, Ochsenhausen (DE); Kai Hasselbach, Hochdorf (DE); Hans Michael Jennewein, Wiesbaden (DE); Bernd Disse, Mainz (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/072,334

(22) Filed: Feb. 6, 2002

(65) Prior Publication Data

US 2003/0105137 A1 Jun. 5, 2003

Related U.S. Application Data

(60) Provisional application No. 60/270,843, filed on Feb. 23, 2001.

(30) Foreign Application Priority Data

Feb. 8, 2001 (DE) .......................... 101 05 628

(51) Int. Cl.$^7$ ..................... A61K 31/445; C07D 401/12
(52) U.S. Cl. ........................ 514/322; 546/199
(58) Field of Search .................... 514/322; 546/199

(56) References Cited

FOREIGN PATENT DOCUMENTS

| | | |
|---|---|---|
| WO | WO 99/24407 | 5/1999 |
| WO | WO 99/40072 | 8/1999 |
| WO | WO 01/14342 | 3/2001 |
| WO | WO 01/23360 | 4/2001 |
| WO | WO 01/34572 | 5/2001 |

OTHER PUBLICATIONS

Tashiro et al. "Inhibitory effect of pulmonary surfactant on Sendai virus infection in rat lungs" CA 125:265108 (1996).*

G.H. Caughey, et al; Bis (5 Amidino–2–Benzimidazolyl) Methane and Related Amidines are Potent, Reversible Inhibitors of Mast Cell Tryptases, Journal of Pharmacology and Experimental Therapeutics, vol. 264, No. 2, 1993, pp. 676–682.

\* cited by examiner

*Primary Examiner*—Ceila Chang
(74) *Attorney, Agent, or Firm*—Robert P. Raymond; Anthony P. Bottino; Timothy X. Witkowski

(57) ABSTRACT

Disclosed are carboxamide-substituted benzimidazole derivatives of general formula (I)

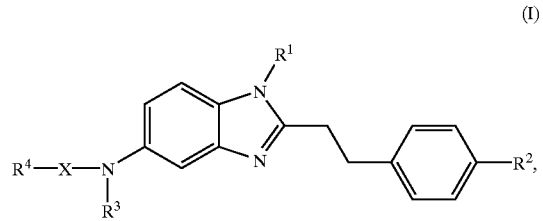

wherein the groups X, $R^1$, $R^2$, $R^3$ and $R^4$ may have the meanings given in the claims and specification, processes for preparing them and the use of carboxamide-substituted benzimidazole derivatives as pharmaceutical compositions, particularly as pharmaceutical compositions with a tryptase-inhibiting activity.

10 Claims, No Drawings

BENZIMIDAZOLE DERIVATIVES, PROCESSES FOR PREPARING THEM AND THEIR USE AS PHARMACEUTICAL COMPOSITIONS

RELATED APPLICATION DATA

This application claims priority to German application 101 05 628.1 filed Feb. 8, 2001 and U.S. provisional application No. 60/270,843 filed Feb. 23, 2001.

TECHNICAL FIELD OF THE INVENTION

The invention relates to benzimidazole derivatives of formula (I)

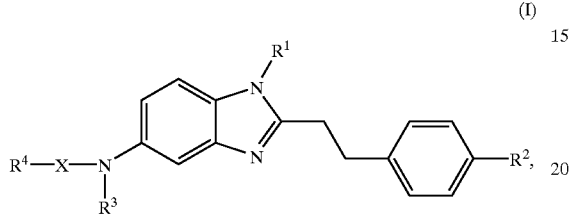

(I)

wherein the groups X, $R^1$, $R^2$, $R^3$ and $R^4$ may have the meanings given in the claims and specification, processes for preparing them and the use of benzimidazole derivatives as pharmaceutical compositions, particularly as pharmaceutical compositions with a tryptase-inhibiting activity.

BACKGROUND TO THE INVENTION

Benzimidazole derivatives are known from the prior art as active substances having valuable pharmaceutical properties. Thus, International Patent Application WO 98/37075 discloses, in addition to other bicyclic heterocycles, benzimidazoles which can be used to good effect for the prevention and treatment of venous and arterial thrombotic diseases, on the basis of their thrombin-inhibiting activity.

In contrast to the use of benzimidazole derivatives as described above and known from the prior art, the aim of the present invention is to prepare new tryptase-inhibitors which can be used, on the basis of their tryptase-inhibiting properties, for the prevention and treatment of inflammatory and/or allergic diseases.

SUMMARY OF THE INVENTION

It is therefore an object of the invention to provide benzimidazole derivatives of formula (I)

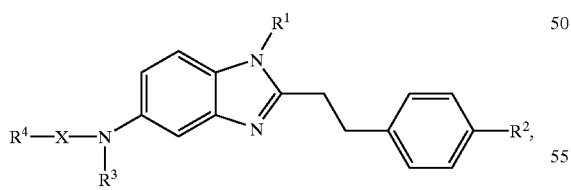

(I)

wherein the groups X, $R^1$, $R^2$, $R^3$ and $R^4$ may have the meanings given in the claims and specification, processes for preparing them and the use of benzimidazole derivatives as pharmaceutical compositions, particularly as pharmaceutical compositions with a tryptase-inhibiting activity.

DETAILED DESCRIPTION OF THE INVENTION

Surprisingly, it has been found that benzimidazole derivatives of general formula (I) wherein the groups $R^1$, $R^2$, $R^3$ and $R^4$ may have the meanings given hereinafter have a tryptase-inhibiting effect and may be used according to the invention for the prevention and treatment of diseases in which tryptase-inhibitors may develop a therapeutic benefit.

The present invention thus relates to benzimidazole derivatives of formula (I)

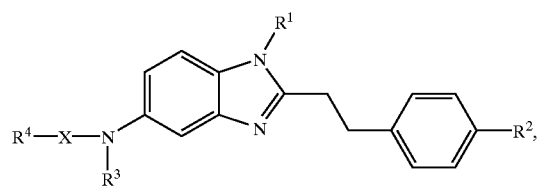

(I)

wherein
$R^1$ denotes a group selected from among $C_1$-$C_{12}$-alkyl, $C_2$-$C_{12}$-alkenyl and $C_2$-$C_{12}$-alkynyl, which may optionally be mono-, di- or trisubstituted by one or more of the groups hydroxy, $C_1$-$C_4$-alkoxy, $CF_3$, phenoxy, COOH, halogen, —CO($C_1$-$C_{12}$-alkoxy), —CO—$NR^5R^6$, —$NR^5R^6$ or $C_1$-$C_1$ 2-alkoxy-phenoxy, or phenyl-$C_1$-$C_{12}$-alkyl, which may optionally be mono-, di- or trisubstituted by one or more of the groups hydroxy, $C_1$-$C_{12}$-alkoxy, carboxy, halogen, $C_1$-$C_{12}$-alkoxycarbonyl or $CF_3$,
or
a 5- or 6-membered, saturated or unsaturated heterocyclic group linked directly or via a $C_1$-$C_{12}$-alkylene bridge, which may contain one or two heteroatoms selected from among oxygen, nitrogen or sulphur and which may optionally be substituted by $C_1$-$C_{12}$-alkyl or benzyl;
$R^2$ denotes —C(=NH)$NH_2$ or —$CH_2$—$NH_2$;
$R^3$ denotes a hydrogen atom or a $C_1$-$C_{12}$-alkyl group which may optionally be mono- or disubstituted by one or two groups selected from among —COOH, —COO—$C_{1-6}$-alkyl, furanyl, benzofuranyl, thiophenyl, benzothiophenyl, anthracenyl, phenyl, pyridyl and naphthyl, while the abovementioned aromatic and heteroaromatic substituents in turn may each be mono-, di- or trisubstituted by one or more of the groups selected from among $C_1$-$C_{12}$-alkyl, $C_1$-$C_{12}$-alkoxy, halogen, —$C_1$-$C_{12}$-alkyl-halogen, —$NH_2$, —NH($C_1$-$C_{12}$-alkyl), —N($C_1$-$C_{12}$-alkyl)$_2$, $NO_2$, hydroxy, —$CF_3$, —NHCO—$C_1$-$C_{12}$-alkyl, —COOH, —COO($C_1$-$C_{12}$-alkyl), —$CONH_2$, —CONH($C_1$-$C_{12}$-alkyl), —CON($C_1$-$C_{12}$-alkyl)$_2$, —CONH($C_1$-$C_{12}$-alkyl)-COO($C_1$-$C_{12}$-alkyl) and phenyl-$C_1$-$C_{12}$-alkyl;
X denotes >C=O, >$CH_2$ or —$CH_2CH_2$—;
$R^4$ denotes a group of formula (A)

(A)

W denotes N or CH;
A denotes $NR^6$ when n=0, and denotes O, $CHR^6$ or $NR^6$ when n=1;
$R^5$ and $R^6$ independently of one another each denote a hydrogen atom or a group of formula —B—(CO)$_m$—, wherein
B denotes a $C_1$-$C_{12}$-alkyl, $C_3$-$C_8$-cycloalkyl, phenyl, naphthyl or a fluorenyl group or a 5- or 6-membered heterocyclic group containing nitrogen, oxygen and/or sulphur, wherein the group B may optionally be substituted in each case by one or more groups selected from among halogen, halo-$C_1$-$C_{12}$-alkyl, halo-$C_1$-$C_{12}$-alkoxy, —OH, $C_1$-$C_{12}$-alkyl, $C_1$-$C_{12}$-alkoxy, phenyl, naphthyl, phenoxy, benzyl, benzyloxy, —CO—O—H, —CO—O—$C_1$-$C_{12}$-alkyl, —$NO_2$, pyrrolidin-1-yl, piperidin-1-yl, —$NH_2$, —NH—$C_1$-$C_{12}$-alkyl, —NH-phenyl, —NH-pyridyl, —N($C_1$-$C_{12}$-alkyl)$_2$ and —C(=NH)$NH_2$, and m denotes 0 or 1, or $R^5$ and $R^6$ together with the nitrogen atom attached form a 5- to 8-membered heterocyclic group, which may be substituted by a group selected from among halogen, halo-$C_1$-$C_{12}$-alkyl, —OH, —$C_1$-$C_{12}$-alkyl, $C_1$-$C_{12}$-alkoxy, phenoxy, benzyloxy, —CO—O—$C_1$-$C_{12}$-alkyl, —$NO_2$, phenyl, pyrrolidin-1-yl, piperidin-1-yl, —$NH_2$, —NH—$C_1$-$C_{12}$-alkyl, —NH-pyridyl, —N($C_1$-$C_{12}$-alkyl)$_2$ and —C(=NH)$NH_2$, n is 0 or 1;

optionally in the form of their tautomers, racemates, enantiomers, diastereomers and mixtures thereof, and optionally the pharmacologically acceptable acid addition salts thereof.

The term alkyl groups (including those which are part of other groups, especially alkoxy), unless otherwise stated, denotes branched and unbranched alkyl groups with 1 to 12 carbon atoms, preferably 1 to 8 carbon atoms, most preferably 1 to 6 carbon atoms, especially 1 to 4 carbon atoms. Examples are: methyl, ethyl, propyl, butyl, pentyl, hexyl, etc. Unless otherwise stated, the above terms propyl, butyl, pentyl or hexyl also include all the possible isomeric forms. For example, the term propyl also includes the two isomeric groups n-propyl and iso-propyl, the term butyl includes n-butyl, iso-butyl, sec. butyl and tert.-butyl, the term pentyl includes iso-pentyl, neopentyl, etc. In some cases common abbreviations are also used to denote the abovementioned alkyl groups, such as Me for methyl, Et for ethyl etc.

The term haloalkyl groups (including those which are part of other groups, especially haloalkoxy), unless otherwise stated, denotes branched and unbranched haloalkyl groups with 1 to 12 carbon atoms, preferably 1 to 6 carbon atoms, especially 1 to 3 carbon atoms, which are substituted by at least one halogen atom, particularly fluorine atom. Fluorinated groups of the formula

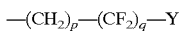

—$(CH_2)_p$—$(CF_2)_q$—Y wherein p denotes 0 or an integer from 1 to 4, q denotes an integer from 1 to 4, and Y denotes hydrogen or fluorine, are preferred.

Examples include: trifluoromethyl, trifluoromethoxy, difluoromethoxy, perfluoroethyl, perfluoropropyl, 2,2,2-trifluoroethyl, 2,2,2-trifluoroethoxy, 1,1,1-trifluoroprop-2-yl, etc.

The term alkenyl groups (including those which are part of other groups) denotes branched and unbranched alkenyl groups having 2 to 12 carbon atoms, preferably 2 to 6 carbon atoms, particularly 2 to 4 carbon atoms, provided that they have at least one double bond, for example the alkyl groups mentioned above as well, provided that they have at least one double bond, such as for example vinyl (provided that no unstable enamines or enolethers are formed), propenyl, iso-propenyl, butenyl, pentenyl and hexenyl.

The term alkynyl groups (including those which are part of other groups) denotes alkynyl groups having 2 to 12 carbon atoms, preferably 2 to 6 carbon atoms, particularly 2 to 4 carbon atoms provided that they have at least one triple bond, e.g. ethynyl, propargyl, butynyl, pentynyl and hexynyl.

The term halogen generally denotes fluorine, chlorine, bromine or iodine.

The term "5- or 6-membered heterocyclic group containing nitrogen, oxygen and/or sulphur" as used in connection with the group B, generally denotes an aromatic or saturated group having 5 or 6 cyclic atoms, wherein at least one cyclic atom is a heteroatom selected from among N, O and S, which may optionally be fused to another cyclic system.

The term "5- to 8-membered heterocyclic group" as used for the group formed by $R^5$ and $R^6$ together with the enclosed nitrogen atom, generally denotes a saturated nitrogen-containing group having 5 to 8 cyclic atoms, which may optionally contain one or more heteroatoms selected from among N, O and S.

The following are mentioned as examples of particular heterocyclic groups: acridinyl, acridonyl, alkylpyridinyl, anthraquinonyl, ascorbyl, azaazulenyl, azabenzanthracenyl, azabenzanthrenyl, azachrysenyl, azacyclazinyl, azaindolyl, azanaphthacenyl, azanaphthalenyl, azaprenyl, azatriphenylenyl, azepinyl, azinoindolyl, azinopyrrolyl, benzacridinyl, benzazapinyl, benzofuryl, benzonaphthyridinyl, benzopyranonyl, benzopyranyl, benzopyronyl, benzoquinolinyl, benzoquinolizinyl, benzothiepinyl, benzothiophenyl, benzylisoquinolinyl, bipyridinyl, butyrolactonyl, caprolactamyl, carbazolyl, carbolinyl, catechinyl, chromenopyronyl, chromonopyranyl, cumarinyl, cumaronyl, decahydroquinolinyl, decahydroquinolonyl, diazaanthracenyl, diazaphenanthrenyl, dibenzazapinyl, dibenzofuranyl, dibenzothiphenyl, dichromylenyl, dihydrofuranyl, dihydroisocumarinyl, dihydroisoquinolinyl, dihydropyranyl, dihydropyridinyl, dihydropyridonyl, dihydropyronyl, dihydrothiopyranyl, diprylenyl, dioxanthylenyl, oenantholactamyl, flavanyl, flavonyl, fluoranyl, fluoresceinyl, furanedionyl, furanochromanyl, furanonyl, furanoquinolinyl, furanyl, furopyranyl, furopyronyl, heteroazulenyl, hexahydropyrazinoisoquinolinyl, hydrofuranyl, hydrofuranonyl, hydroindolyl, hydropyranyl, hydropyridinyl, hydropyrrolyl, hydroquinolinyl, hydrothiochromenyl, hydrothiophenyl, indolizidinyl, indolizinyl, indolonyl, isatinyl, isatogenyl, isobenzofuranedionyl, isobenzofuranyl, isochromanyl, isoflavonyl, isoindolinyl, isoindolobenzazapinyl, isoindolyl, isoquinolinyl, isoquinuclidinyl, lactamyl, lactonyl, maleimidyl, monoazabenzonaphthenyl, naphthalenyl, naphthimidazopyridindionyl, naphthindolizinedionyl, naphthodihydropyranyl, naphthofuranyl, naphthyridinyl, oxepinyl, oxindolyl, oxolenyl, perhydroazolopyridinyl, perhydroindolyl, phenanthraquinonyl, phthalideisoquinolinyl, phthalimidyl, phthalonyl, piperidinyl, piperidonyl, prolinyl, parazinyl, pyranoazinyl, pyranoazolyl, pyranopyranedionyl, pyranopyridinyl, pyranoquinolinyl, pyranopyrazinyl, pyranyl, pyrazolopyridinyl, pyridinethionyl, pyridinonaphthalenyl, pyridinopyridinyl, pyridinyl, pyridocolinyl, pyridoindolyl, pyridopyridinyl, pyridopyrimidinyl, pyridopyrrolyl, pyridoquinolinyl, pyronyl, pyrrocolinyl, pyrrolidinyl, pyrrolizidinyl, pyrrolizinyl, pyrrolodioazinyl, pyrrolonyl, pyrrolopyrmidinyl, pyrroloquinolonyl, pyrrolyl, quinacridonyl, quinolinyl, quinolizidinyl, quinolizinyl, quinolonyl, quinuclidinyl, rhodaminyl, spirocumaranyl, succinimidyl, sulpholanyl, sulpholenyl, tetrahydrofuranyl, tetrahydroisoquinolinyl, tetrahydropyranyl, tetrahydropyridinyl, tetrahydrothiapyranyl, tetrahydrothiophenyl, tetrahydrothipyranonyl, tetrahydrothipyranyl, tetronyl, thiaphenyl, thiachromanyl, thiadecalinyl, thianaphthenyl, thiapyranyl, thiapyronyl, thiazolopyridinyl, thienopyridinyl, thienopyrrolyl, thienothiophenyl, thiepinyl, thiochromenyl, thiocumarinyl, thiopyranyl, triazaanthracenyl, triazinoindolyl, triazolopyridinyl, tropanyl, xanthenyl, xanthonyl, xanthydrolyl, adeninyl, alloxanyl, alloxazinyl, anthranilyl, azabenzanthrenyl, azabenzonaphthenyl, azanaphthacenyl, azaphenoxazinyl, azapurinyl, azinyl, azoloazinyl, azolyl, barbituric acid, benzazinyl, benzimidazolethionyl, benzimidazolonyl, benzisothiazolyl, benzisoxazolyl, benzocinnolinyl, benzodiazocinyl, benzodioxolanyl; benzodioxolyl, benzopyridazinyl, benzothiazepinyl, benzothiazinyl, benzothiazolyl, benzoxazinyl, benzoxazolinonyl, benzoxazolyl, cinnolinyl, depsidinyl, diazaphenanthrenyl, diazepinyl, diazinyl, dibenzoxazepinyl, dihydrobenzimidazolyl, dihydrobenzothiazinyl, dihydrooxazolyl, dihydropyridazinyl, dihydropyrimidinyl, dihydrothiazinyl, dioxanyl, dioxenyl, dioxepinyl, dioxinonyl, dioxolanyl, dioxolonyl, dioxopiperazinyl, dipyrimidopyrazinyl, dithiolanyl, dithiolenyl, dithiolyl, flavinyl, furopyrimidinyl, glycocyamidinyl, guaninyl, hexahydropyrazinoisoquinolinyl, hexahydropyridazinyl, hydantoinyl, hydroimidazolyl, hydroparazinyl, hydropyrazolyl, hydropyridazinyl, hydropyrimidinyl, imidazolinyl, imidazolyl, imidazoquinazolinyl, imidazothiazolyl, indazolebenzopyrazolyl, indoxazenyl, inosinyl, isoalloxazinyl, isothiazolyl, isoxazolidinyl, isoxazolinonyl, isoxazolinyl, isoxazolonyl, isoxazolyl, lumazinyl, methylthyminyl, methyluracilyl, morpholinyl, naphthimidazolyl, oroticyl, oxathianyl, oxathiolanyl, oxazinonyl, oxazolidinonyl, oxazolidinyl, oxazolidonyl, oxazolinonyl, oxazolinyl, oxazolonyl, oxazolopyrimidinyl, oxazolyl, perhydrocinnolinyl, perhydropyrroloazinyl, perhydropyrrolothiazinyl, perhydrothiazinonyl, perimidinyl, phenazinyl, phenothiazinyl, phenoxathiinyl, phenoxazinyl, phenoxazonyl, phthalazinyl, piperazinedionyl, piperazinodionyl, polyquinoxalinyl, pteridinyl, pterinyl, purinyl, pyrazinyl, pyrazolidinyl, pyrazolidonyl, pyrazolinonyl, parazolinyl, pyrazolobenzodiazepinyl, pyrazolonyl, pyrazolopyrimidinyl, pyrazolotriazinyl, pyrazolyl, pyridazinyl, pyridazonyl, pyridopyrazinyl, pyridopyrimidinyl, pyrimidinethionyl, pyrimidinyl, pyrimidionyl, pyrimidoazepinyl, pyrimidopteridinyl, pyrrolobenzodiazepinyl, pyrrolodiazinyl, pyrrolopyrimidinyl, quinazolidinyl, quinazolinonyl, quinazolinyl, quinoxalinyl, sultamyl, sultinyl, sultonyl, tetrahydrooxazolyl, tetrahydropyrazinyl, tetrahydropyridazinyl, tetrahydroquinoxalinyl, tetrahydrothiazolyl, thiazepinyl, thiazinyl, thiazolidinonyl, thiazolidinyl, thiazolinonyl, thiazolinyl, thiazolobenzimidazolyl, thiazolyl, thienopyrimidinyl, thiazolidinonyl, thyminyl, triazolopyrimidinyl, uracilyl, xanthinyl, xylitolyl, azabenzonapththenyl, benzofuroxanyl, benzothiadiazinyl, benzotriazepinonyl, benzotriazolyl, benzoxadiazinyl, dioxadiazinyl, dithiadazolyl, dithiazolyl, furazanyl, furoxanyl, hydrotriazolyl, hydroxytrizinyl, oxadiazinyl, oxadiazolyl, oxathiazinonyl, oxatriazolyl, pentazinyl, pentazolyl, pentazinyl, polyoxadiazolyl, sydonyl, tetraoxanyl, tetrazepinyl, tetrazinyl, tetrazolyl, thiadiazinyl, thiadiazinlyl, thiadiazolyl, thiadioxazinyl, thiatriazinyl, thiatriazinyl, thiatriazolyl, triazepinyl, triazinoindolyl, triazinyl, triazolinedionyl, triazolinyl, triazolyl, trioxanyl, triphenodioxazinyl, triphenodithiazinyl, trithiadiazepinyl, trithianyl or trioxolanyl.

Examples of particularly preferred 5-, 6- or 7-membered, saturated or unsaturated heterocycles which may contain nitrogen, oxygen or sulphur as heteroatoms include, for example, furan, tetrahydrofuran, tetrahydrofuranone, γ-butyrolactone, α-pyran, γ-pyran, dioxolan, tetrahydropyran, dioxan, thiophene, dihydrothiophene, thiolan, dithiolan, pyrrole, pyrroline, pyrrolidine, pyrazole, pyrazoline, pyrazolidine, imidazole, imidazoline, imidazolidine, triazole, tetrazole, pyridine, piperidine, pyridazine, pyrimidine, pyrazine, piperazine, triazine, tetrazine, morpholine, thiomorpholine, diazepan, oxazole, isoxazole, oxazine, thiazole, isothiazole, thiadiazole, oxadiazole and pyrazolidine, unless otherwise specified in the definitions, wherein the heterocyclic group may be substituted as stated in the definitions.

Compounds of formula (I), wherein X denotes >C=O, W denotes N and A denotes NR$^6$, are preferred.

m is preferably 0, and n is preferably 1.

R$^5$ is preferably naphthyl, particularly naphth-2-yl, pyridyl, particularly pyrid-2-yl or pyrid-3-yl or a phenyl group optionally substituted by one or two halogen atoms, particularly selected from the formula

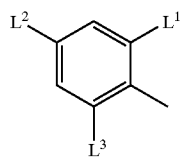

wherein

L$^1$ denotes a fluorine, chlorine, bromine or iodine atom, and
L$^2$ and L$^3$ independently of one another each denote a hydrogen, fluorine or chlorine atom.

Preferred compounds according to the invention are the compounds of formula (I), wherein R$^1$ denotes a C$_1$-C$_6$-alkyl group, particularly methyl, ethyl, propyl or butyl, which may optionally be mono, di- or trisubstituted by one or more of the groups hydroxy, C$_1$-C$_4$-alkoxy, CF$_3$, phenoxy, COOH, halogen, —CO(C$_1$-C$_4$-alkoxy), —CO—NR$^5$R$^6$, —NR$^5$R$^6$ or C$_1$-C$_4$-alkoxy-phenoxy.

Also preferred are compounds of formula (I), wherein R$^4$ denotes a group of formula (A), A denotes NR$^6$, R$^5$ denotes a C$_1$-C$_4$-alkyl, phenyl, naphthyl, fluorenyl, pyridyl, pyrrolidinyl or benzyl group, while these groups may each optionally be substituted by one, two or three groups selected from among halogen, —OH, halo-C$_1$-C$_4$-alkyl, halo-C$_1$-C$_4$-alkoxy, C$_1$-C$_4$-alkyl, C$_1$-C$_4$-alkoxy, phenyl, naphthyl, phenoxy, benzyl, benzyloxy, —CO—OH, —CO—O—C$_1$-C$_4$-alkyl, —NO$_2$, pyridyl, pyrrolidin-1-yl, piperidin-1-yl, —NH$_2$, —NH—C$_1$-C$_4$-alkyl, and R$^6$ denotes a hydrogen atom or a C$_1$-C$_4$-alkyl group.

Particularly preferred are the compounds of formula (I), wherein R$^1$ denotes methyl, ethyl or propyl; and
R$^4$ denotes a group of formula (A1)

(A1)

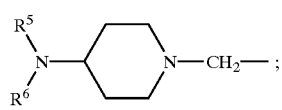

X denotes >C=O;
R$^5$ denotes a hydrogen atom or a C$_1$-C$_4$-alkyl, C$_1$-C$_4$-alkanoyl, phenyl, naphthyl, fluorenyl, anthracenyl, pyridyl, pyrrolidinyl or benzyl group, while these groups may each optionally be substituted by one or more groups, preferably one or two groups selected from among halogen, halo-$C_1$-$C_4$-alkyl, halo-$C_1$-$C_4$-alkoxy, —OH, $C_1$-$C_4$-alkyl, $C_1$-$C_4$-alkoxy, phenyl, naphthyl, phenoxy, benzyl, benzyloxy, —CO—O—$C_1$-$C_4$-alkyl, —$NO_2$, pyridyl, pyrrolidin-1-yl, piperidin-1-yl, —$NH_2$, —NH—$C_1$-$C_4$-alkyl, —N($C_1$-$C_4$-alkyl)$_2$ and —C(=NH)$NH_2$, and $R^6$ denotes a hydrogen atom or a $C_1$-$C_4$-alkyl group.

Also preferred are benzimidazole derivatives of general formula (I), wherein $R^1$ denotes $C_1$-$C_4$-alkyl, which may optionally be mono, di- or trisubstituted by one or more of the groups hydroxy, $C_1$-$C_4$-alkoxy, $CF_3$, phenoxy, COOH, halogen, —CO($C_1$-$C_4$-alkoxy or $C_1$-$C_4$-alkoxy-phenoxy, $R^2$ denotes —C(=NH)$NH_2$ or —$CH_2$—$NH_2$;

$R^3$ denotes methyl, —$CH_2$—COOH, —$CH_2$—COO—$C_1$-$C_4$-alkyl, naphthylmethyl, benzyl or pyridylmethyl, which may be substituted at the particular aromatic and heteroaromatic ring by a group selected from among $C_1$-$C_6$-alkyl, —$NH_2$, —NH($C_1$-$C_4$-alkyl) and —N($C_1$-$C_4$-alkyl)$_2$, $R^4$ denotes a group of formula (A), wherein A is $NR^6$;

X denotes >C=O;

$R^5$ denotes methyl, ethyl, propyl, butyl, phenyl, naphthyl, pyridyl or benzyl, which may optionally be substituted by one or two groups selected from among halogen, trifluoromethyl, trifluoromethoxy, methyl, —OH, methoxy, —$NO_2$, phenyl, naphthyl, pyrrolidin-1-yl, —$NH_2$, —NH-methyl, —N(methyl)$_2$, —NH-ethyl, —N(ethyl)$_2$ and —C(=NH)$NH_2$, $R^6$ denotes hydrogen, methyl, ethyl, propyl or butyl, optionally in the form of their tautomers, racemates, enantiomers, diastereomers and mixtures thereof, and optionally the pharmacologically acceptable acid addition salts thereof.

Particularly preferred are benzimidazole derivatives of formula (I), wherein $R^1$ denotes methyl, ethyl, propyl or butyl, preferably methyl;

$R^2$ denotes —C(=NH)$NH_2$ or —$CH_2$—$NH_2$, preferably —C(=NH)$NH_2$;

$R^3$ denotes methyl, —$CH_2$—COOH, —$CH_2$—COO-ethyl, naphthylmethyl, benzyl or pyridylmethyl, $R^4$ denotes a group of formula (A1);

X denotes >C=O;

$R^5$ denotes phenyl, naphthyl, pyridyl or benzyl, which may optionally be substituted by one or two groups selected from among fluorine, chlorine, bromine, iodine, trifluoromethyl, methyl, —OH, methoxy and phenyl, $R^6$ denotes hydrogen or methyl, optionally in the form of their tautomers, racemates, enantiomers, diastereomers and mixtures thereof, and optionally the pharmacologically acceptable acid addition salts thereof.

Also particularly preferred are benzimidazole derivatives of formula (I), wherein $R^1$ denotes methyl;

$R^2$ denotes —C(=NH)$NH_2$;

$R^3$ denotes methyl, —$CH_2$—COOH, —$CH_2$—COO-ethyl, naphthylmethyl, benzyl or pyridylmethyl;

$R^4$ denotes a group of formula (A1);

X denotes >C=O;

$R^5$ denotes phenyl, naphthyl, pyridyl or benzyl, which may optionally be substituted by one or two groups selected from among fluorine, chlorine, bromine, iodine, trifluoromethyl, methyl, —OH, methoxy and phenyl, $R^6$ denotes hydrogen or methyl, optionally in the form of their tautomers, racemates, enantiomers, diastereomers and mixtures thereof, and optionally the pharmacologically acceptable acid addition salts thereof.

Of particular importance according to the invention are benzimidazole derivatives of formula (I), wherein $R^1$ denotes methyl;

$R^2$ denotes —C(=NH)$NH_2$;

$R^3$ denotes methyl, —$CH_2$—COOH, —$CH_2$—COO-ethyl, benzyl, naphth-1-ylmethyl or pyrid-4-ylmethyl;

$R^4$ denotes a group of formula (A1);

X denotes >C=O;

optionally in the form of their tautomers, racemates, enantiomers, diastereomers and mixtures thereof, and optionally the pharmacologically acceptable acid addition salts thereof.

Particularly preferred are the compounds of formulae (IA) and (IB)

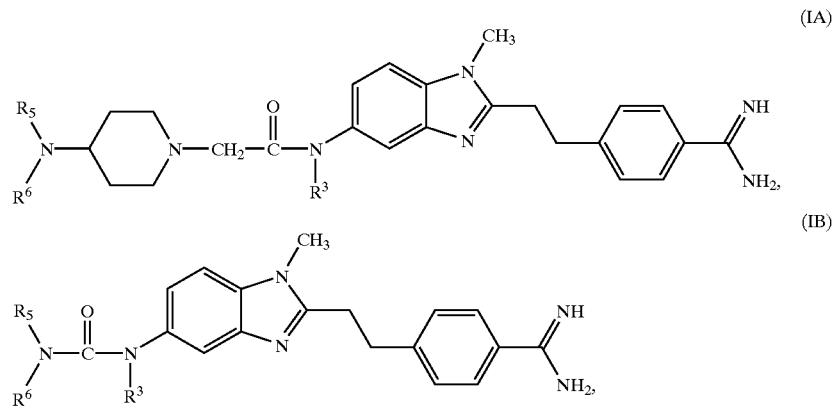

wherein in each case $R^3$ denotes hydrogen, —$CH_2$—COOH, —$CH_2$—COO-ethyl, methyl, butyl, benzyl, pyridylmethyl or naphthalinylmethyl, wherein the aromatic groups may be substituted in each case by $C_1$-$C_6$-alkyl, —$NO_2$, —$NH_2$, —NH—$C_1$-$C_4$-alkyl, or —N($C_1$-$C_4$-alkyl)$_2$;

$R^5$ denotes a $C_1$-$C_4$-alkyl, $C_1$-$C_4$-alkanoyl, phenyl, pyridyl, benzoyl or pyridylcarbonyl group, while these groups may each optionally be substituted by one or more, preferably one, two or three, particularly one or two groups selected from among halogen, —OH, —$C_1$-$C_4$-alkyl, $C_1$-$C_4$-alkoxy, phenyl, naphthyl, phenoxy, benzyl, benzyloxy, —CO—O—$C_1$-$C_4$-alkyl, —$NO_2$, phenyl, —$NH_2$, —NH—$C_1$-$C_4$-alkyl and —N($C_1$-$C_4$-alkyl)$_2$, and $R^6$ denotes a hydrogen atom or a methyl group, optionally in the form of their tautomers, racemates, enantiomers, diastereomers and mixtures thereof, and optionally the pharmacologically acceptable acid addition salts thereof.

In addition to the abovementioned compounds of general formula (I) the present invention also relates to compounds which are only converted into the therapeutically effective compounds of general formula (I) by the body after being taken by the patient, on the basis of a functionality which can be cleaved in vivo. Such compounds are known as prodrugs. According to another aspect the invention therefore relates to prodrugs of general formula (II)

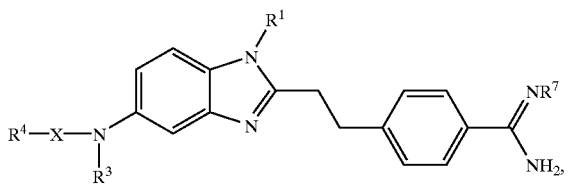

(II)

wherein

X, $R^1$, $R^3$ and $R^4$ are as hereinbefore defined and $R^7$ denotes hydroxy, —COO—$C_1$-$C_{12}$alkyl, —COO—$C_1$-$C_{12}$-haloalkyl, —CO-phenyl, —CO-pyridyl, —COO-phenyl or —COO—$C_1$-$C_8$-alkyl-phenyl, wherein in the abovementioned groups the phenyl ring may be substituted in each case by $C_1$-$C_4$-alkyl, $C_1$-$C_4$-alkoxy, OH, halogen, —$NH_2$, $C_1$-$C_4$-alkyl-NH, di-($C_1$-$C_4$-alkyl)N or $CF_3$, optionally in the form of their tautomers, racemates, enantiomers, diastereomers and mixtures thereof, and optionally the pharmacologically acceptable acid addition salts thereof.

Preferred are prodrugs of formula (II), wherein $R^7$ denotes hydroxy, —COO—$C_1$-$C_6$-alkyl, —COO—$C_1$-$C_6$-haloalkyl, —CO-phenyl, —CO-pyridyl, —COO-phenyl or —COO—$C_1$-$C_6$-alkyl-phenyl, wherein in the abovementioned group the phenyl ring may be substituted in each case by $C_1$-$C_4$-alkyl, $C_1$-$C_4$-alkoxy, OH, halogen or $CF_3$, optionally in the form of their tautomers, racemates, enantiomers, diastereomers and mixtures thereof, and optionally the pharmacologically acceptable acid addition salts thereof.

Particularly preferred are prodrugs of general formula (II), wherein $R^7$ denotes hydroxy, methoxycarbonyl, ethoxycarbonyl, propyloxycarbonyl, 2,2,2-trichloroethoxycarbonyl, butyloxycarbonyl, benzoyl, benzyloxycarbonyl or nicotinoyl, optionally in the form of their tautomers, racemates, enantiomers, diastereomers and mixtures thereof, and optionally the pharmacologically acceptable acid addition salts thereof.

The present invention is further directed to the use of the compounds of general formula (I) as hereinbefore defined and the prodrugs of general formula (II) for preparing a pharmaceutical composition for the treatment of diseases in which tryptase inhibitors may be of therapeutic benefit.

It is preferred according to the invention to use compounds of general formula (I) for the purpose mentioned above, for preparing a pharmaceutical composition for the prevention and/or treatment of inflammatory and/or allergic diseases. It is particularly preferable to use the compounds of general formula (I) as mentioned above to prepare a pharmaceutical composition for the prevention and/or treatment of bronchial asthma, allergic rhinitis, allergic conjunctivitis, atopic dermatitis, urticaria, allergic otitis, allergic gastro-intestinal disorders, Crohn's disease, ulcerative colitis, anaphylactic shock, septic shock, shock lung (ARDS) and arthritis.

It is also advantageous to use the compounds of general formula (I) as mentioned above for preparing a pharmaceutical composition for the prevention and/or treatment of diseases with reconstruction processes in the airways and the lung parenchyma such as chronic (obstructive) bronchitis and interstitial lung diseases such as idiopathic lung fibrosis, fibrosing alveolitis, sarcoidosis and histiocytosis X and other fibrosing diseases such as scarring, and also collagenoses such as lupus erythematodes and scierodermia as well as arteriosclerosis, psoriasis and neoplasia.

The substituted benzimidazole derivatives of formula (I) as well as the prodrugs of general formula (II) may be obtained by various methods of synthesis. Possible approaches based on and using conventional methods of chemical synthesis are hereinafter described by way of example. Diagram 1 shows one possible method of synthesising the basic benzimidazole structure of the compounds according to the invention.

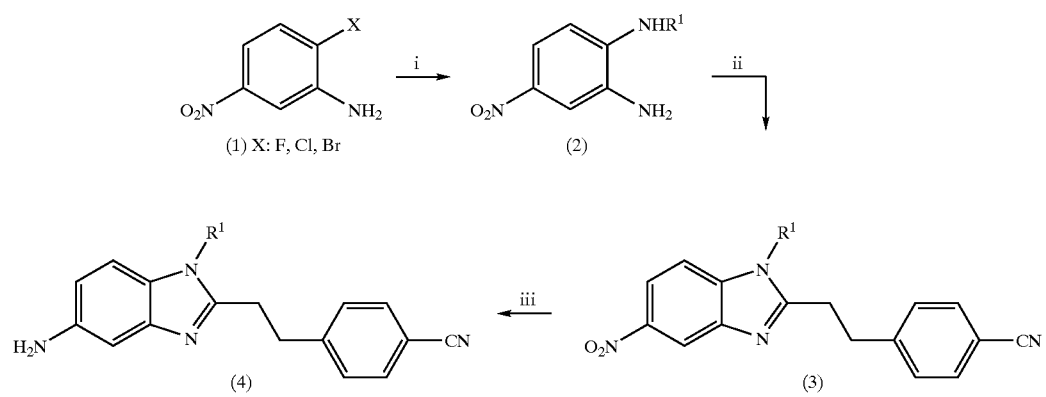

Diagram 1:

Starting from the 2-halo-5-nitro-anilines (1) aminolysis may be carried out first to obtain the diaminonitrobenzoles (2) according to Diagram 1 (step i). The aminolysis of the compounds (1) with the primary amines R¹—NH₂ is carried out in suitable organic solvents such as for example dimethylsulphoxide, N,N-dimethylformamide, N-methylpyrrolidone, acetone or optionally also in water or alcohols at ambient temperature or in a temperature range from 30-80° C., preferably 40-50° C.

The reaction of the compounds (2) with p-cyanophenylpropionic acid leads to the nitrobenzimidazoles (3, step ii) in the presence of dehydrating reagents. The reaction is optionally carried out in a solvent or mixture of solvents such as acetic acid, methylene chloride, dimethylformamide, benzene, toluene, chlorobenzene, tetrahydrofuran, benzene/tetrahydrofuran or dioxan. Suitable dehydrating agents include for example isobutyl chloroformate, tetraethyl orthocarbonate, trimethyl orthoacetate, 2,2-dimethoxypropane, tetramethoxysilan, phosphorus oxychloride, thionylchloride, trimethylchlorosilane, phosphorus trichloride, phosphorus pentoxide, ethyl 1,2-dihydro-2-ethoxy-quinoline-1-carboxylate (EEDQ), i-propyl 1,2-dihydro-2-1-propyloxy-quinoline-1-carboxylate (IIDQ), N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride. It may be appropriate to add a base such as pyridine, 4-dimethylaminopyridine, N-methyl-morpholine or triethylamine. The reaction is usually carried out at temperatures between 0 and 150° C., preferably at temperatures between 20 and 120° C.

The nitrobenzimidazole derivatives (3) obtained according to the procedure described above may be reductively converted into the aminobenzimidazoles (4) (step iii, Diagram 1). The reduction of the nitro group to form the compounds (3) is carried out for example by catalytic hydrogenation in organic solvents such as for example methanol, ethanol, isopropanol, tetrahydrofuran, optionally also in admixture with dimethylformamide, ethyl acetate, dioxan or acetic acid, at elevated hydrogen pressure or at normal pressure at temperatures between 0-50° C., preferably at 20-40° C. Suitable catalysts are conventional hydrogenation catalysts. Palladium and Raney nickel are preferred. According to the invention, palladium is preferred. Palladium on charcoal (5%) is particularly preferred as the catalyst. An alternative method of reducing the nitro compounds (3) envisages the use of reduction agents such as Na₂S₂O₄ or SnCl₂. This reaction is carried out in protic, water-miscible organic solvents such as short-chained alcohols (methanol, ethanol, isopropanol) or in a mixture of the abovementioned solvents with water, optionally with acetic acid, dimethylformamide or ethyl acetate. The reaction is normally carried out at elevated temperature, preferably by refluxing the solvent or solvent mixture in question. After the reaction of the starting compounds (3) is complete, the mixture is worked up in the usual way. The compounds (4) may be purified for example by crystallisation from nonpolar organic solvents such as diethylether, petroleum ether, optionally mixed with ethyl acetate.

Starting from the benzimidazoles (4) which may be obtained according to Diagram 1, the compounds (5) according to Diagram 2 are obtained by reaction with the compounds R³—Nu, where Nu denotes a nucleofugic leaving group such as for example chlorine, bromine, iodine, methanesulphonate, methyltriflate, p-toluenesulphonate etc. Alternatively, the compounds (5) may be obtained starting from the compounds (4) by the method of reductive amination by reacting with correspondingly substituted ketones or aldehydes under reductive conditions.

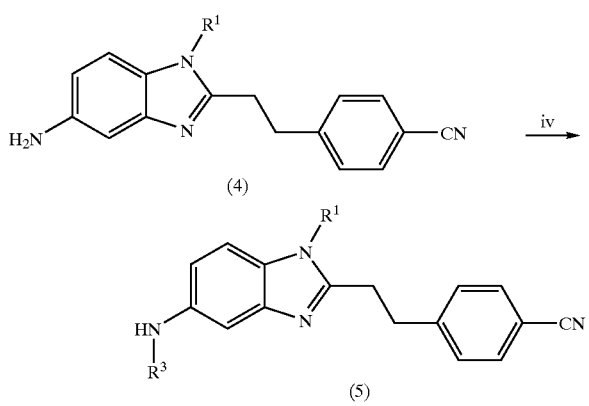

Diagram 2:

In order to react the compounds (4) with R³—Nu according to step iv the following procedure may be used. A compound (4) is dissolved in a polar solvent, such as dimethylformamide, dimethylactamide, methylene chloride, tetrahydrofuran, preferably dimethylformamide and most preferably anhydrous, possibly absolute dimethylformamide. The solution thus obtained is combined with a base and the corresponding alkylating agent R³—Nu. The base used may be an alkali or alkaline earth metal carbonate of lithium, sodium, potassium, calcium such as sodium carbonate, lithium carbonate, potassium carbonate, calcium carbonate and preferably potassium carbonate. It is also possible to use the alkali or alkaline earth metal hydroxides of lithium, sodium, potassium, magnesium, calcium, but preferably sodium hydroxide, potassium hydroxide, lithium hydroxide and calcium hydroxide in alcohol or water. The reaction mixture is stirred for 0.5-8 h, preferably 1-4 h at elevated temperature, preferably at 50-120° C., particularly at the reflux temperature of the solvent used. After the reaction is complete the mixture is worked up in the usual way and the crude product obtained is purified by crystallisation or chromatography on silica gel.

If the compounds (5) are obtained from the compounds (4) by reductive amination, the following procedure is used. The compound (4) is dissolved in a suitable solvent such as for example dichloromethane, dichloroethane, methanol, ethanol, tetrahydrofuran or toluene, and at between 0-60° C., preferably at 20-40° C., the corresponding carbonyl compound is added in the presence of an acid, preferably a carboxylic acid, most preferably a short-chained carboxylic acid, particularly acetic acid. Then a suitable reduction agent is added. Suitable reduction agents which may be used according to the invention are Na[HB(OAc)₃], Na[BH₃CN], NaBH₄, Pd/C—H₂, preferably Na[HB(OAc)₃]. After working up in the usual way the product is purified by crystallisation or chromatography on silica gel.

The intermediates of general formula (III) wherein n is 1 may be obtained from the compounds (5), as shown in Diagram 3, by acylation (step va) or alkylation (step vb).

Scheme 3

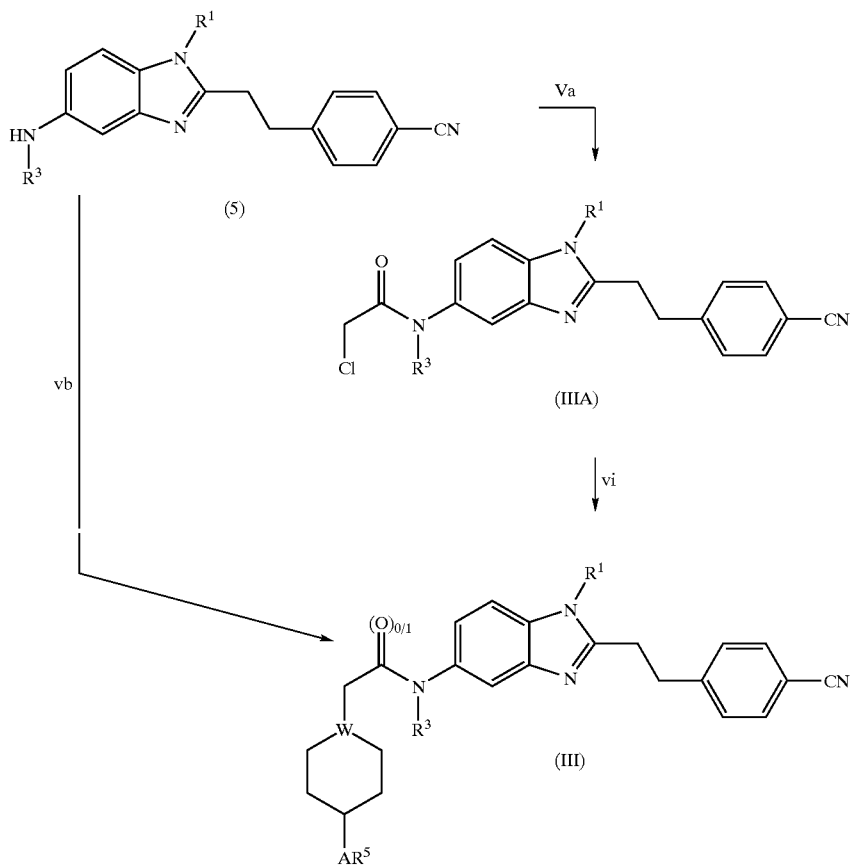

Diagram 3:

The reaction of the compounds (5) with the chloroacetic acid to obtain the intermediates of general formula (III) may be carried out in a solvent or mixture of solvents such as methylene chloride, dimethylformamide, benzene, toluene, chlorobenzene, tetrahydrofuran, benzene/tetrahydrofuran or dioxan, optionally in the presence of a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methyl-morpholine or triethylamine, conveniently at temperatures between 0 and 150° C., preferably at temperatures between 0 and 100° C. Alternatively, the intermediates of general formula (III) may also be obtained by standard methods by reacting with alkylating reagents $R^4$—$CH_2X^1$ (with $X^1$: halide, mesylate, tosylate, etc.) or activated carboxylic acid derivatives $R^4$—$COX^2$ (with $X^2$: halide, alkoxy, etc.) in the abovementioned solvents or mixtures of solvents in the presence of bases such as pyridine, 4-dimethylaminopyridine, N-methyl-morpholine or triethylamine.

The compounds (IIIA) may be reacted with the amines according to step vi to form the intermediates (III). The compound (IIIA) is dissolved in a polar solvent, such as dimethylformamide, dimethylactamide, methylene chloride, tetrahydrofuran, preferably dimethylformamide and most preferably anhydrous, possibly absolute dimethylformamide. The solution thus obtained is combined with a base and the corresponding amine. The base used may be an alkali or alkaline earth metal carbonate of lithium, sodium, potassium, calcium such as sodium carbonate, lithium carbonate, potassium carbonate, calcium carbonate and preferably potassium carbonate. The reaction mixture is stirred for 0.5-8 h, preferably 1-4 h at elevated temperature, preferably at 50-120° C., particularly at the reflux temperature of the solvent used. After the reaction is complete the mixture is worked up in the usual way and the crude product obtained is purified by crystallisation or chromatography on silica gel.

The intermediates of general formula (III) wherein $R^6$ denotes hydrogen and is 0, [?] may be obtained from the compounds (5), as shown in Diagram 4, by reacting with the corresponding isocyanates. The compounds of formula (III) wherein $R^6$ is other than hydrogen may be obtained by alkylation with an alkylating reagent $R^6$—$X^3$ (with $X^3$: halide, mesylate, tosylate, etc.) or by reductive amination by the methods described in connection with Diagram 2.

Scheme 4

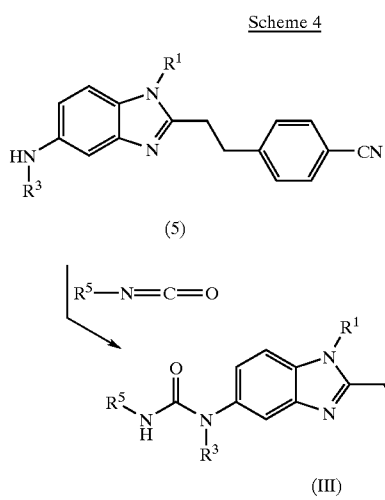

Diagram 4:

The compounds of formula (I) according to the invention may be obtained from the intermediates (III) according to step vii in Diagram 5.

Alternatively, the compounds of general formula (I) may be obtained by reacting a compound of general formula (III) with sulphur nucleophiles such as e.g. hydrogen sulphide, ammonium or sodium sulphide, sodium hydrogen sulphide, carbon disulphide, thioacetamide or bistrimethylsilylthioether, optionally in the presence of bases such as triethylamine, ammonia, sodium hydride or sodium alkoxide in solvents such as methanol, ethanol, water, tetrahydrofuran, pyridine, dimethylformamide or 1,3-dimethyl-imidazolidin-2-one at 20-100° C., and subsequent treatment with a suitable methylating agent such as e.g. methyliodide or dimethylsulphate in a solvent such as acetonitrile or acetone at temperatures between −10 and 50° C., but preferably at 0-20° C., and subsequent treatment with ammonia, ammonium carbonate or ammonium chloride in a suitable alcohol, such as for example methanol, ethanol, isopropanol etc. at temperatures between −10 and 50° C., but preferably at 0-20° C.

Moreover, the compounds of general formula (I) according to the invention may be obtained by treating a compound of general formula (III) with lithium hexamethyl disilazide in a suitable organic solvent such as e.g. tetrahydrofuran at temperatures between −20 and 50° C., but preferably at 0-20° C. and subsequently hydrolysing with dilute hydrochloric acid at 0-5° C.

Schema 5

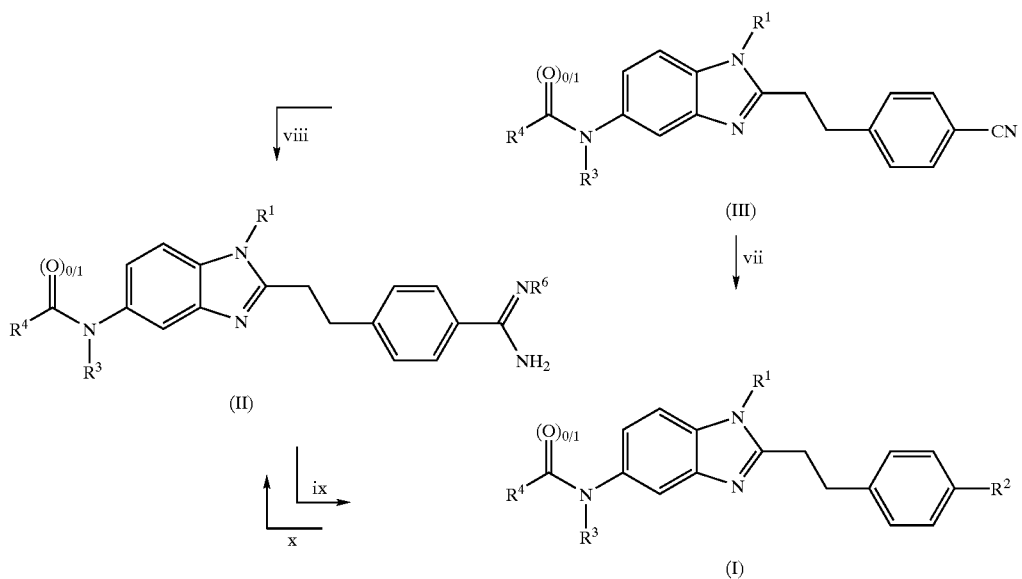

Diagram 5:

In order to prepare the compounds of general formula (I) according to the invention wherein $R^2$ denotes —C(=NH)NH$_2$, various procedures may be used.

A compound of general formula (I) is obtained for example by treating a compound of general formula (III) with a corresponding alcohol such as methanol, ethanol, n-propanol, isopropanol or benzylalcohol optionally mixed with another organic solvent such as for example chloroform, nitrobenzene or toluene in the presence of an acid such as hydrochloric acid or by reacting a corresponding amide with a trialkyloxonium salt such as triethyloxonium tetrafluoroborate in a solvent such as methylene chloride, tetrahydrofuran or dioxan at temperatures between −10 and 50° C., but preferably at 0-20° C. and subsequent aminolysis with alcoholic ammonia solution, for example.

Another alternative method of obtaining compounds of general formula (I) is by treating a compound of general formula (III) with ammonium chloride and trimethylaluminium in a suitable organic solvent such as e.g. toluene at temperatures between 20 and 150° C., but preferably at 110° C.

Compounds of general formula (I) wherein $R^2$ denotes —CH$_2$—NH$_2$ may be obtained from the intermediates (III) for example by catalytic hydrogenation on Raney nickel. These reactions are preferably carried out in protic organic solvents such as short-chained alcohols (methanol, ethanol or isopropanol) at temperatures between 10-40° C., preferably at 20-30° C. under normal pressure.

A compound of general formula (II) is obtained for example by treating a compound of general formula (III, Diagram 3, step vii) with hydroxylamine in the presence of carbonates or alkoxides of alkali or alkaline earth metals in solvents such as methanol, ethanol, n-propanol or isopropanol optionally in admixture with dioxan or tetrahydrofuran. The alkoxides may be prepared from the respective alkali metals or metal hydrides and the corresponding alcohol. The reaction is preferably carried out at 20-100° C., most preferably at the boiling temperature of the solvent used.

Compounds of general formula (II) may alternatively be obtained by treating a compound of general formula (III) with a corresponding alcohol such as methanol, ethanol, n-propanol, isopropanol or benzylalcohol in the presence of an acid such as hydrochloric acid or by reacting a corresponding amide with a trialkyloxonium salt such as triethyloxonium-tetrafluoroborate in a solvent such as methylene chloride, tetrahydrofuran or dioxan at temperatures between −10 and 50° C., but preferably at 0-20° C. and subsequently treating with hydroxylamine in the presence of bases in a suitable alcohol, such as methanol, ethanol, isopropanol etc. at temperatures between −10 and 50° C., but preferably at 0-20° C.

A compound of general formula (I) is obtained for example by treating a compound of general formula (II), (Diagram 3, step viii) with hydrogen in the presence of hydrogenation catalysts such as Raney nickel or rhodium/aluminium oxide in water or methanol, optionally with the addition of acids such as hydrochloric acid or methanesulphonic acid or by treating with hydrogen in the presence of palladium/charcoal in acetic acid/acetic anhydride at 20-50° C. and 1-5 bar hydrogen pressure, preferably at ambient temperature and normal pressure.

The acyl- or alkoxycarbonyl prodrugs (II) of the compound of general formula (I) are obtained by reacting the compounds of general formula (I) with the corresponding acid chlorides in the presence of bases such as e.g. triethylamine, N-methyl morpholine, diethylisopropylamine or DBU in a suitable solvent such as methylene chloride, chloroform, tetrahydrofuran, acetonitrile, dimethylformamide or dimethylsulphoxide.

In accordance with their central role in the synthesis of the compounds of general formula (I) according to the invention as well as the synthesis of the prodrugs of general formula (II), a further aspect of the present invention is directed to the intermediates of general formula (III)

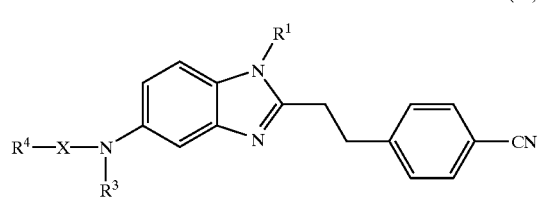

(III)

wherein the groups X, R1, R3 and R4 are as hereinbefore defined.

The compounds of general formula (III) are valuable intermediates for preparing the benzimidazole derivatives of general formula (I) according to the invention as well as the prodrugs of general formula (II) according to the invention.

By virtue of their pharmacological properties, the compounds according to the invention may be used as pharmaceutical compositions, particularly as pharmaceutical compositions with a tryptase-inhibiting activity. They may be used wherever tryptase inhibitors may be of therapeutic benefit.

It is preferred according to the invention to use compounds of general formula (I) to prepare a pharmaceutical composition for the prevention and/or treatment of inflammatory and/or allergic diseases. It is particularly preferable to use the compounds of general formula (I) as mentioned above to prepare a pharmaceutical composition for the prevention and/or treatment of bronchial asthma, allergic rhinitis, allergic conjunctivitis, atopic dermatitis, urticaria, allergic otitis, allergic gastro-intestinal disorders, Crohn's disease, ulcerative colitis, anaphylactic shock, septic shock, shock lung (ARDS) and arthritis.

It is also advantageous to use the compounds of general formula (I) as mentioned above for preparing a pharmaceutical composition for the prevention and/or treatment of fibroses such as lung fibrosis, fibrosing alveolitis and scarring, collagenoses such as lupus erythematodes and sclerodermia as well as arteriosclerosis, psoriasis and neoplasia.

Procedures by way of example for preparing the compounds according to the invention will be described in more detail hereinafter. The Examples which follow serve solely as a detailed illustration without restricting the subject matter of the invention.

EXAMPLE 1

N-{2-[2-(4-Amidinophenyl)-ethyl]-1-methyl-benzimidazol-5-yl}-N-[naphth-1-ylmethyl]-2-(4-phenylamino-piperid-1-yl)-acetamide, Dihydrochloride

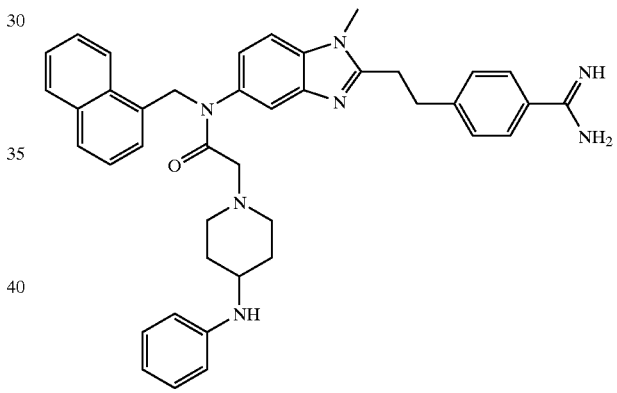

a) $N^1$-methyl-1,2-diamino-4-nitrobenzene 2-fluoro-5-nitro-aniline (15.0 g, 160 mmol) is taken up in 480 mL of 40% aqueous methylamine solution and stirred for 2.5 days at ambient temperature and for 2 h at 40-50° C. The mixture is diluted with water, the solid matter is filtered off, washed with water and dried.

Yield: 26 g (97%); melting point: 171-173° C.

b) 2-[2-(4-Cyanophenyl)-ethyl]-1-methyl-5-nitro-benzimidazole $N^1$-methyl-1,2-diamino-4-nitrobenzene (8.3 g, 49.6 mmol) and p-cyano-phenyl-propionic acid (9.6 g, 55 mmol) are taken up in 90 mL POCl$_3$, and refluxed for 1.5 h. After cooling the excess POCl$_3$ is decomposed with ice water. The mixture is made alkaline with NH$_3$ with stirring and cooling and stirred for 1 h at ambient temperature. The solid matter is filtered off, washed with water and recrystallised from DMF.

Yield: 11.7 g (76.4%); melting point: 202-204° C.

c) 5-Amino-2-[2-(4-cyanophenyl)-ethyl]-1-methyl-benzimidazole

2-[2-(4-Cyanophenyl)-ethyl]-1-methyl-5-nitro-benzimidazole (5.5 g, 18 mmol) in 150 mL THF and 75 mL methanol is hydrogenated in the presence of 1.0 g of 5% Pd/C at ambient temperature under normal pressure. The catalyst is filtered off, the filtrate is evaporated, not quite to dryness, diluted with 100 mL of acetonitrile and evaporated down to a residual volume of 30 mL. The crystal slurry is cooled and filtered. The crystals are washed with cold acetonitrile and ether.

Yield: 4.7 g (94%); melting point: 187-192° C.

d) 2-[2-(4-Cyanophenyl)-ethyl]-1-methyl-5-naphth-1-ylmethylamino-benzimidazole 1.0 g (3.6 mmol) of 5-amino-2-[2-(4-cyanophenyl)-ethyl]-1-methyl-benzimidazole and 1-naphthylaldehyde (0.33 mL, 3.6 mmol) are combined with 0.22 mL acetic acid in 25 mL of dichloromethane at ambient temperature and Na[HB(Oac)$_3$] is added thereto with stirring. The mixture is stirred for 1 h at ambient temperature, covered with water, carefully acidified with concentrated aqueous hydrochloric acid and then made alkaline with 4N NaOH solution. The organic phase is separated off, dried and evaporated down. The product is chromatographed over silica gel and optionally crystallised from diethyl ether.

Yield: 0.8 g (67%); melting point: 112-114° C.

e) N-{2-[2-(4-Cyanophenyl)-ethyl]-1-methyl-benzimidazol-5-yl}-N-(naphth-1-ylmethyl)-2-chloroacetamide A mixture of 4.0 g (9.6 mmol) of 2-[2-(4-cyanophenyl)-ethyl]-1-methyl-5-naphth-1-ylmethylamino-benzimidazole and 1.1 mL (10.0 mmol) of N-methylmorpholine in 80 ml of dichloromethane was cooled to 10° C. A solution of 0.8 mL (10.0 mmol) of chloroacetylchloride in 15 ml of dichloromethane was added dropwise to the solution within 15 min. The mixture was then stirred for 30 min at ambient temperature. It was washed with water and dilute potassium carbonate solution, dried and concentrated by evaporation. The product is chromatographed on silica gel.

Yield: 4.1 g, 87%.

f) N-{2-[2-(4-Cyanophenyl)-ethyl]-1-methyl-benzimidazol-5-yl}-N-(naphth-1-ylmethyl)-2-(4-phenylamino-piperid-1-yl)-acetamide A solution of 2.1 g (4.3 mmol) of N-{2-[2-(4-cyanophenyl)-ethyl]-1-methyl-benzimidazol-5-yl}-N-(naphth-1-ylmethyl)-2-chloroacetamide, 1.5 g (6.0 mmol) of 4-phenylamino-1-piperidine and 2.2 mL of N-methylmorpholine in 15 mL of dimethylformamide was stirred for 8 hours at 70-80° C. The mixture was then poured onto ice, extracted with ethyl acetate and washed with water, dried and distilled off. The product was chromatographed on silica gel.

Yield: 2.0 g (73%).

g) N-{2-[2-(4-Amidinophenyl)-ethyl]-1-methyl-benzimidazol-5-yl}-N-[naphth-1-ylmethyl]-2-(4-phenylamino-piperid-1-yl)-acetamide, dihydrochloride N-{2-[2-(4-Cyanophenyl)-ethyl]-1-methyl-benzimidazol-5-yl}-N-methyl-[3-(4-cyanophenyl)-propionamide] (1.3 g, 2.9 mmol) is taken up in 50 mL of a saturated ethanolic HCl solution cooled to 0° C. The mixture is stirred until the educt is fully dissolved and then left overnight at 0-5° C. The ethanol is distilled off at a maximum of 40° C. and the residue is taken up in 40 mL of an ethanolic ammonia solution saturated at 0° C. The mixture is stirred for 2 h at ambient temperature, then for 3 h at 50-60°, another 10 mL of saturated ammonia solution are added, the resulting solution is refluxed for 2 hours and kept overnight at ambient temperature. The inorganic salts precipitated are filtered off, the filtrate is evaporated down and the residue is chromatographed on silica gel.

Yield: 1.0 g (62%);

$^1$H-NMR (250 MHz, CD$_3$OD): δ=8.21-6.55 (19H, aryl-H), 5.52 (2H, s, napht.-CH2-N), 3.87 (2H, CH2—CO), 4.74 (3H, s, N—CH3), 3.24 (4H, aryl-CH2CH2—), 3.63, 2.36-1.64 (9H, m, pip.CH2; CH).

EXAMPLE 2

N-{2-[2-(4-Amidinophenyl)-ethyl]-1-methyl-benzimidazol-5-yl}-N-[naphth-1-ylmethyl]-2-{4-[N-methyl-N-(3-hydroxypropyl)-amino]-piperid-1-yl}-acetamide, Trihydrochloride

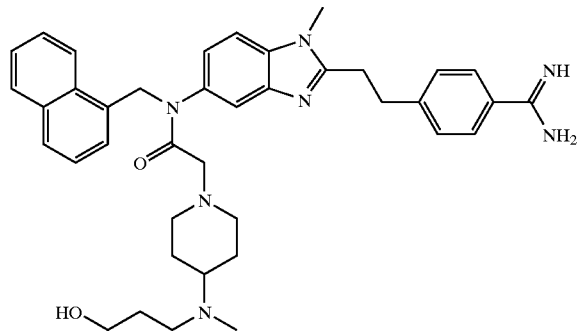

a) N-{2-[2-(4-Cyanophenyl)-ethyl]-1-methyl-benzimidazol-5-yl}-N-(naphth-1-ylmethyl)-2-{4-[N-methyl-N-(3-hydroxypropyl)-amino]-piperid-1-yl}-acetamide The compound is synthesised starting from the N-{2-[2-(4-cyanophenyl)-ethyl]-1-methyl-benzimidazol-5-yl}-N-(naphth-1-ylmethyl)-2-chloroacetamide obtained according to Example 1, step e, 4-[N-methyl-N-(3-hydroxypropyl)-amino]-1-piperidine and potassium carbonate analogously to the method described in Example 1, step f.

Yield: 92%.

b) N-{2-[2-(4-Amidinophenyl)-ethyl]-11-methyl-benzimidazol-5-yl}-N-[naphth-1-ylmethyl]-2-{4-[N-methyl-N-(3-hydroxypropyl)-amino]-piperid-1-yl}-acetamide, Trihydrochloride The title compound is synthesised as described for Example 1 step g starting from N-{2-[2-(4-cyanophenyl)-ethyl]-1-methyl-benzimidazol-5-yl}-N-(naphth-1-ylmethyl)-2-{4-[N-methyl-N-(3-hydroxypropyl)-amino]-piperid-1-yl}-acetamide.

Yield: 37%.

$^1$H-NMR (250 MHz, DMSO-d$_6$): δ=9.38; 9.16 (4H, 2s, NH$_2$—C=N$^+$H$_2$), 8.19-6.66 (14H, m, aryl/naphthyl-H), 5.36 (2H, s, napht.-CH$_2$—N), 3.63 (3H, s, NCH$_3$), 3.43 (2H, t, J=6.5 Hz, OCH$_2$—), 3.32 (2H, s, CH$_2$C=O), 3.13 (4H, s, aryl-CH$_2$CH$_2$), 2.93, 2.56 (3H, N—CH$_3$), 2.17-1.39 (14H, m, pip. CH$_2$, CH, OH).

EXAMPLE 3

N-{2-[2-(4-Amidinophenyl)-ethyl]-1-methyl-benzimidazol-5-yl}-N-(4-tert-butylphenylmethyl)-2-[4-(2-pyridylamino)-piperid-1-yl]-acetamide, Dihydrochloride

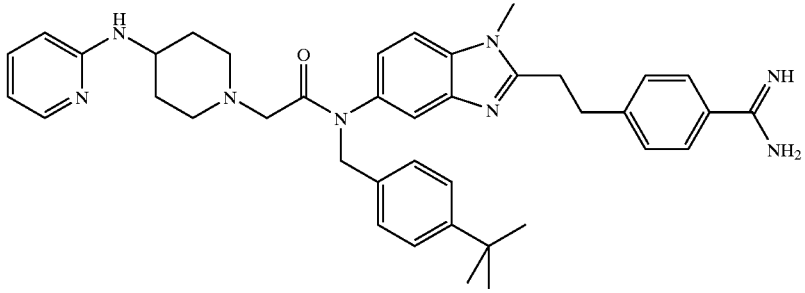

a) 2-[2-(4-cyanophenyl)-ethyl]-1-methyl-5-(4-tert-butylphenyl methyl)-amino-benzimidazole The reductive amination is carried out starting from the 5-amino-2-[2-(4-cyanophenyl)-ethyl]-1-methyl-benzimidazole obtained according to Example 1, step c, and 4-tert-butyl-benzaldehyde analogously to the method described in Example 1, step d.

Yield: 60% b) N-{2-[2-(4-cyanophenyl)-ethyl]-11-methyl-benzimidazol-5-yl}-N-(4-tert-butylphenylmethyl)-2-chloroacetamide Analogously to Example 1, step e, 2-[2-(4-cyanophenyl)-ethyl]-1-methyl-5-(4-tert-butylphenylmethyl)-amino-benzimidazole was reacted with chloroacetylchloride. The product was purified by chromatography on silica gel. Yield: 100% c) N-{2-[2-(4-cyanophenyl)-ethyl]-1-methyl-benzimidazol-5-yl}-N-(4-tert-butylphenylmethyl)-2-[4-(2-pyridylamino)-piperid-1-yl]-acetamide N-{2-[2-(4-cyanophenyl)-ethyl]-1-methyl-benzimidazol-5-yl}-N-(4-tert-butylphenylmethyl)-2-chloroacetamide was reacted with 4-(2-pyridyl)-amino-piperidine according to Example 1, step f. The product was purified by chromatography on silica gel.

Yield: 56% d) N-{2-[2-(4-Amidinophenyl)-ethyl]-1-methyl-benzimidazol-5-yl}-N-(4-tert-butylphenylmethyl)-2-[4-(2-pyridylamino)-piperid-1-yl]-acetamide, Dihydrochloride Analogously to Example 1, step g, N-{2-[2-(4-cyanophenyl)-ethyl]-1-methyl-benzimidazol-5-yl}-N-(4-tert-butylphenylmethyl)-2-[4-(2-pyridylamino)-piperid-1-yl]-acetamide was reacted to obtain the title compound. The product was purified by chromatography on silica gel.

Yield: 53%.

$^1$H-NMR (250 MHz, CD$_3$OD): δ=7.89-6.45 (15H, m, aryl/pyridyl-H), 4.93 (2H, s, aryl-CH$_2$—N), 3.74 (3H, s, N—CH$_3$), 3.64, 3.26 (4H, m, aryl-CH$_2$CH$_2$), 2.45-1.62 (11H, m, pip.-CH$_2$, CH, CH$_2$C=O), 1.25 [9H, s, C(CH$_3$)$_3$].

EXAMPLE 4

N-{2-[2-(4-Amidinophenyl)-ethyl]-1-methyl-benzimidazol-5-yl}-N-(methyl)-2-[4-(2-chlorophenylamino)-piperid-1-yl]-acetamide-dihydrochloride

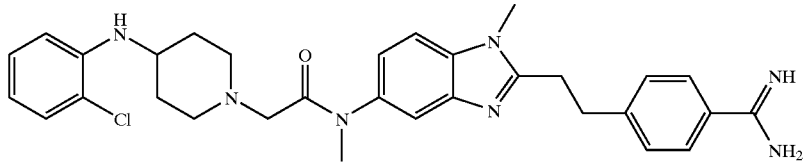

a) N-{2-[2-(4-cyanophenyl)-ethyl]-1-methyl-benzimidazol-5-yl}-trifluoroacetamide Trifluoroacetic acid anhydride (15.0 mL) was added dropwise to 27.6 g (100.0 mmol) of 5-amino-2-[2-(4-cyanophenyl)-ethyl]-1-methyl-benzimidazole in 270 mL of pyridine at 5-20° C. The mixture was stirred for 15 min at ambient temperature and diluted with water. The solid matter was filtered off and washed with water. The crystals were dissolved in 300 mL of ethyl acetate with heating, dried and evaporated until not quite dry. The filtrate was cooled, the solid precipitate was filtered off and washed with diethylether.

Yield: 32.2 g (86%); melting point: 225-228° C.

b) 2-[2-(4-cyanophenyl)-ethyl]-1-methyl-5-methylamino-benzimidazole 11.2 g (30.0 mmol) of N-{2-[2-(4-cyanophenyl)-ethyl]-1-methyl-benzimidazol-5-yl}-trifluoroacetamide, 10.5 g (76.0 mmol) of potassium carbonate and 2.0 mL of methyliodide were stirred for 3 hours in 80 mL of dimethylsulphoxide at 40-50° C. Then the mixture was diluted with 100 mL of ethyl acetate, poured onto water and extracted. The organic phase is again washed with water, dried and concentrated by evaporation. The residue is chromatographed on silica gel. The methylated trifluoroacetamide is taken up in MeOH, with 10 mL of conc. aqueous ammonia solution and stirred for 4 h at 30-40° C. The methanol is distilled off, the residue is taken up in 75 mL of ethyl acetate, washed with water, dried and evaporated down. The product is crystallised from diethylether.

Yield: 6.5 g (75%); melting point: 155-158° C.

c) N-{2-[2-(4-cyanophenyl)-ethyl]-11-methyl-benzimidazol-5-yl}-N-methyl-2-chloroacetamide According to Example 1, step e, 2-[2-(4-cyanophenyl)-ethyl]-11-methyl-5-methylamino-benzimidazole was reacted with chloroacetyl chloride. The product was purified by chromatography on silica gel.

Yield: 68%.

d) N-{2-[2-(4-cyanophenyl)-ethyl]-1-methyl-benzimidazol-5-yl}-N-(methyl)-2-[4-(2-chlorophenyl)amino-piperid-1-yl]-acetamide Analogously to Example 1, step f, N-{2-[2-(4-cyanophenyl)-ethyl]-1-methyl-benzimidazol-5-yl}-N-methyl-2-chloroacetamide was reacted with 4-(2-chlorophenyl)-amino-1-piperidine. The product was purified by chromatography on silica gel.

Yield: 86%.

e) N-{2-[2-(4-Amidinophenyl)-ethyl]-1-methyl-benzimidazol-5-yl}-N-methyl-2-[4-(2-chlorophenyl)amino-piperid-1-yl]-acetamide, Dihydrochloride N-{2-[2-(4-cyanophenyl)-ethyl]-1-methyl-benzimidazol-5-yl}-N-(methyl)-2-[4-(2-chlorophenyl)amino-piperid-1-yl]-acetamide was reacted analogously to Example 1, step g to obtain the title compound. The residue was chromatographed on silica gel.

Yield: 1.1 g (73%).

$^1$H-NMR (250 MHz, DMSO-$d_6$): δ=9.40, 9.05 (4H.2s, $NH_2$—C=$N^+H_2$), 7.90-6.52 (11H, m, aryl-H), 4.76 (1H, d, J=8.0 Hz, NH—CH), 3.81 (3H, N—$CH_3$), 3.31 (4H, s, aryl-$CH_2CH_2$—), 2.80 (2H, s, $CH_2$C=O), 3.22 (3H, s, N—$CH_3$), 3.35, 2.86-1.38 (9H, m, pip.-$CH_2$, CH).

EXAMPLE 5
N-{2-[2-(4-Amidinophenyl)-ethyl]-1-methyl-benzimidazol-5-yl}-N-(naphth-1-ylmethyl)-N'-benzyl-urea, Hydrochloride

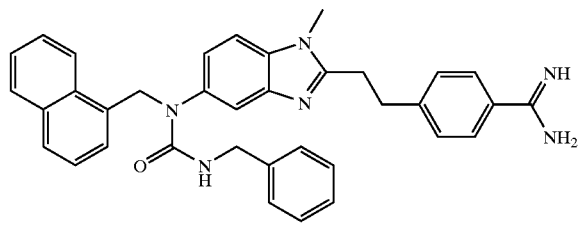

a) 1-{2-[2-(4-cyanophenyl)-ethyl]-1-methyl-benzimidazol-5-yl}-1-(naphth-1-ylmethyl)-3-benzylurea 1.37 g (3.3 mmol) of 2-[2-(4-cyanophenyl)-ethyl]-1-methyl-5-naphth-1-ylmethylamino-benzimidazole obtained from Example 1, step d was dissolved in 20 mL of dichloromethane at ambient temperature [and] 0.40 g (3.0 mmol) of benzyl isocyanate are added dropwise to the solution. The mixture was then stirred for 6 h at 50° C. and left to stand overnight. The solution was evaporated down in vacuo using the rotary evaporator and purified by column chromatography on silica gel.

Yield: 1.28 g (71%).

b) 1-{2-[2-(4-Amidinophenyl)-ethyl]-1-methyl-benzimidazol-5-yl}-1-(naphth-1-ylmethyl)-3-benzylurea, Hydrochloride 1.25 g (2.27 mmol) of 1-{2-[2-(4-cyanophenyl)-ethyl]-1-methyl-benzimidazol-5-yl}-1-(naphth-1-ylmethyl)-3-benzylurea were reacted according to Example 1, step g to form the amidine. The product was purified by column chromatography on silica gel.

Yield: 1.23 g (67%).

$^1$H-NMR (250 MHz, $CD_3OD$): δ=8.33-6.85 (19H, m, aryl-H), 5.40 (2H, s, naphth.-$CH_2$—N), 4.34 (2H, s, aryl-$CH_2$—N), 3.63 (3H, s, $NCH_3$), 3.19 (4H, s, aryl-$CH_2CH_2$—).

The following Tables list further compounds of general formula (I) synthesised according to the invention analogously to the Examples described hereinbefore.

TABLE 1

| No | —$R^3$ | —$AR^5$ | Chemical name |
|---|---|---|---|
| 6 | naphth-1-ylmethyl | 2-pyridylamino-N-methyl | N-{2-[2-(4-Amidinophenyl)-ethyl]-1-methyl-benzimidazol-5-yl}-N-[naphth-1-ylmethyl]-2-[4-(2-pyridylamino-piperid-1-yl]-acetamide, dihydrochloride |
| 7 | naphth-1-ylmethyl | 2-pyridylcarboxamide | N-{2-[2-(4-Amidinophenyl)-ethyl]-1-methyl-benzimidazol-5-yl}-N-[naphth-1-ylmethyl]-2-[4-(2-pyridylcarboxylic acid amide)-piperid-1-yl]-acetamide, dihydrochloride |

TABLE 1-continued

| No | —R³ | —AR⁵ | Chemical name |
|---|---|---|---|
| 8 | naphth-1-ylmethyl | N-methyl benzamide | N-{2-[2-(4-Amidinophenyl)-ethyl]-1-methyl-benzimidazol-5-yl}-N-[naphth-1-ylmethyl]-2-[4-benzoic acid amide-piperid-1-yl]-acetamide, dihydrochloride |
| 9 | naphth-1-ylmethyl | benzyl | N-{2-[2-(4-Amidinophenyl)-ethyl]-1-methyl-benzimidazol-5-yl}-N-[naphth-1-ylmethyl]-2-[4-(benzyl)-piperid-1-yl]-acetamide, dihydrochloride |
| 10 | naphth-1-ylmethyl | N-methyl-4-chloroaniline | N-{2-[2-(4-Amidinophenyl)-ethyl]-1-methyl-benzimidazol-5-yl}-N-[naphth-1-ylmethyl]-2-[4-(4-chlorophenylamino)-piperid-1-yl]-acetamide, dihydrochloride |
| 11 | naphth-1-ylmethyl | N-methyl-3-chloroaniline | N-{2-[2-(4-Amidinophenyl)-ethyl]-1-methyl-benzimidazol-5-yl}-N-[naphth-1-ylmethyl]-2-[4-(3-chlorophenylamino)-piperid-1-yl]-acetamide, dihydrochloride |
| 12 | naphth-1-ylmethyl | N-methyl-2-chloroaniline | N-{2-[2-(4-Amidinophenyl)-ethyl]-1-methyl-benzimidazol-5-yl}-N-[naphth-1-ylmethyl]-2-[4-(2-chlorophenylamino)-piperid-1-yl]-acetamide, dihydrochloride |
| 13 | naphth-1-ylmethyl | N-methyl-4-dimethylaminoaniline | N-{2-[2-(4-Amidinophenyl)-ethyl]-1-methyl-benzimidazol-5-yl}-N-[naphth-1-ylmethyl]-2-[4-(4-dimethylaminophenyl-amino)-piperid-1-yl]-acetamide, trihydrochloride |
| 14 | naphth-1-ylmethyl | N-methyl-4-methoxyaniline | N-{2-[2-(4-Amidinophenyl)-ethyl]-1-methyl-benzimidazol-5-yl}-N-[naphth-1-ylmethyl]-2-[4-(4-methoxyphenylamino)-piperid-1-yl]-acetamide, dihydrochloride |

TABLE 1-continued

| No | —R³ | —AR⁵ | Chemical name |
|---|---|---|---|
| 15 | naphth-1-ylmethyl | –CH₂–NH₂ | N-{2-[2-(4-Amidinophenyl)-ethyl]-1-methyl-benzimidazol-5-yl}-N-[naphth-1-ylmethyl]-2-[4-amino-piperid-1-yl]-acetamide, trihydrochloride |
| 16 | naphth-1-ylmethyl | 2-pyridinyloxy | N-{2-[2-(4-Amidinophenyl)-ethyl]-1-methyl-benzimidazol-5-yl}-N-[naphth-1-ylmethyl]-2-[4-(2-pyridinoxy)-piperid-1-yl]-acetamide, dihydrochloride |
| 17 | naphth-1-ylmethyl | N-methyl-4-benzyloxyphenylamino | N-{2-[2-(4-Amidinophenyl)-ethyl]-1-methyl-benzimidazol-5-yl}-N-[naphth-1-ylmethyl]-2-[4-(4-benzyloxy-phenylamino)-piperid-1-yl]-acetamide, dihydrochloride |
| 18 | naphth-1-ylmethyl | N-methyl-4-hydroxyphenylamino | N-{2-[2-(4-Amidinophenyl)-ethyl]-1-methyl-benzimidazol-5-yl}-N-[naphth-1-ylmethyl]-2-[4-(4-hydroxyphenylamino)-piperid-1-yl]-acetamide, dihydrochloride |
| 19 | naphth-1-ylmethyl | 2-pyridyl-N-methyl-amino | N-{2-[2-(4-Amidinophenyl)-ethyl]-1-methyl-benzimidazol-5-yl}-N-[naphth-1-ylmethyl]-2-[4-(2-pyridyl-N-methyl-amino)-piperid-1-yl]-acetamide, dihydrochloride |
| 20 | naphth-1-ylmethyl | 2-pyridylmethyl | N-{2-[2-(4-Amidinophenyl)-ethyl]-1-methyl-benzimidazol-5-yl}-N-[naphth-1-ylmethyl]-2-[4-(2-pyridylmethyl)-piperid-1-yl]-acetamide, dihydrochloride |
| 21 | naphth-1-ylmethyl | ethyl N-methyl-N-propionate (dimethylamino) | N-{2-[2-(4-Amidinophenyl)-ethyl]-1-methyl-benzimidazol-5-yl}-N-[naphth-1-ylmethyl]-2-[4-(ethyl N-methyl-N-propionate)-piperid-1-yl]-acetamide, trihydrochloride |

TABLE 1-continued

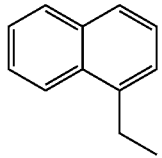

| No | —R³ | —AR⁵ | Chemical name |
|---|---|---|---|
| 22 | 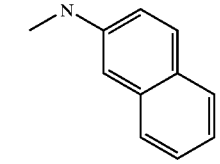 | 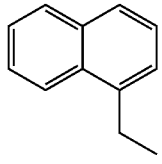 | N-{2-[2-(4-Amidinophenyl)-ethyl]-1-methyl-benzimidazol-5-yl}-N-[naphth-1-ylmethyl]-2-[4-(2-naphthylamino)-piperid-1-yl]-acetamide, dihydrochloride |
| 23 | 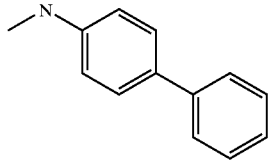 | 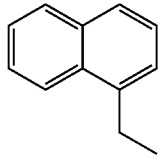 | N-{2-[2-(4-Amidinophenyl)-ethyl]-1-methyl-benzimidazol-5-yl}-N-[naphth-1-ylmethyl]-2-[4-(4-biphenylamino)-piperid-1-yl]-acetamide, dihydrochloride |
| 24 | 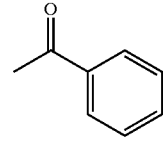 | 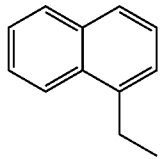 | N-{2-[2-(4-Amidinophenyl)-ethyl]-1-methyl-benzimidazol-5-yl}-N-[naphth-1-ylmethyl]-2-[4-(phenylcarbonyl)-piperid-1-yl]-acetamide, dihydrochloride |
| 25 | 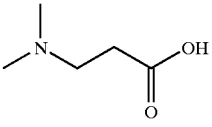 | 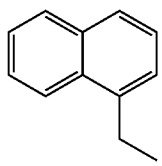 | N-{2-[2-(4-Amidinophenyl)-ethyl]-1-methyl-benzimidazol-5-yl}-N-[naphth-1-ylmethyl]-2-[4-(N-methyl-N-propionic acid)-piperid-1-yl]-acetamide, diacetate |
| 26 | 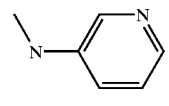 | 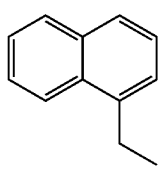 | N-{2-[2-(4-Amidinophenyl)-ethyl]-1-methyl-benzimidazol-5-yl}-N-[naphth-1-ylmethyl]-2-[4-(3-pyridylamino)-piperid-1-yl]-acetamide, dihydrochloride |
| 27 | 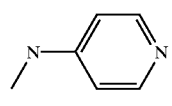 | 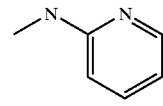 | N-{2-[2-(4-Amidinophenyl)-ethyl]-1-methyl-benzimidazol-5-yl}-N-[naphth-1-ylmethyl]-2-[4-(4-pyridylamino)-piperid-1-yl]-acetamide, dihydrochloride |
| 28 | —CH₃ | 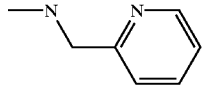 | N-{2-[2-(4-Amidinophenyl)-ethyl]-1-methyl-benzimidazol-5-yl}-N-methyl-2-[4-(2-pyridylamino)-piperid-1-yl]-acetamide, dihydrochloride |
| 29 | —CH₃ | 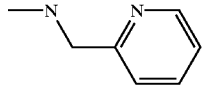 | N-{2-[2-(4-Amidinophenyl)-ethyl]-1-methyl-benzimidazol-5-yl}-N-methyl-2-[4-(2-pyridylmethylamino)-piperid-1-yl]-acetamide, dihydrochloride |

TABLE 1-continued

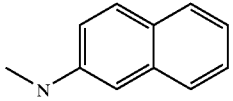

| No | —R³ | —AR⁵ | Chemical name |
|---|---|---|---|
| 30 | —CH₃ | 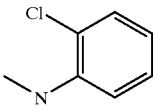 | N-{2-[2-(4-Amidinophenyl)-ethyl]-1-methyl-benzimidazol-5-yl}-N-methyl-2-[4-(2-naphthylamino)-piperid-1-yl]-acetamide, dihydrochloride |
| 31 | —CH₃ | 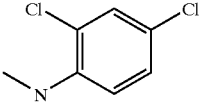 | N-{2-[2-(4-Amidinophenyl)-ethyl]-1-methyl-benzimidazol-5-yl}-N-methyl-2-[4-(2-chlorophenylamino)-piperid-1-yl]-acetamide, dihydrochloride |
| 32 | —CH₃ | 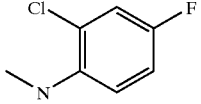 | N-{2-[2-(4-Amidinophenyl)-ethyl]-1-methyl-benzimidazol-5-yl}-N-methyl-2-[4-(2,4-dichlorophenylamino)-piperid-1-yl]-acetamide, dihydrochloride |
| 33 | —CH₃ | 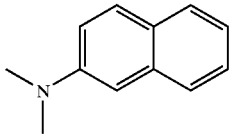 | N-{2-[2-(4-Amidinophenyl)-ethyl]-1-methyl-benzimidazol-5-yl}-N-methyl-2-[4-(2-chloro-4-fluorophenylamino)-piperid-1-yl]-acetamide, dihydrochloride |
| 34 | —CH₃ | 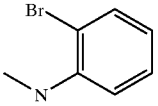 | N-{2-[2-(4-Amidinophenyl)-ethyl]-1-methyl-benzimidazol-5-yl}-N-methyl-2-[4-(2-naphthyl-N-methylamino)-piperid-1-yl]-acetamide, dihydrochloride |
| 35 | —CH₃ | 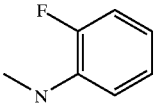 | N-{2-[2-(4-Amidinophenyl)-ethyl]-1-methyl-benzimidazol-5-yl}-N-methyl-2-[4-(2-bromophenylamino)-piperid-1-yl]-acetamide, dihydrochloride |
| 36 | —CH₃ | | N-{2-[2-(4-Amidinophenyl)-ethyl]-1-methyl-benzimidazol-5-yl}-N-methyl-2-[4-(2-fluorophenylamino)-piperid-1-yl]-acetamide, dihydrochloride |
| 37 | —CH₃ | 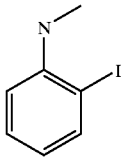 | N-{2-[2-(4-Amidinophenyl)-ethyl]-1-methyl-benzimidazol-5-yl}-N-methyl-2-[4-(2-iodophenylamino)-piperid-1-yl]-acetamide, dihydrochloride |
| 38 | —CH₃ | 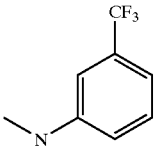 | N-{2-[2-(4-Amidinophenyl)-ethyl]-1-methyl-benzimidazol-5-yl}-N-methyl-2-[4-(2-trifluoromethylphenylamino)-piperid-1-yl]-acetamide, dihydrochloride |

TABLE 1-continued

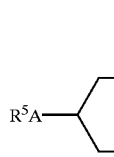

| No | —R³ | —AR⁵ | Chemical name |
|---|---|---|---|
| 39 | —CH₃ | 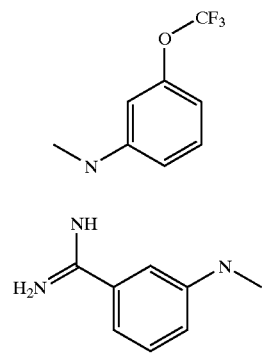 | N-{2-[2-(4-Amidinophenyl)-ethyl]-1-methyl-benzimidazol-5-yl}-N-methyl-2-[4-(2-trifluoromethoxyphenylamino)-piperid-1-yl]-acetamide, dihydrochloride |
| 40 | —CH₃ | 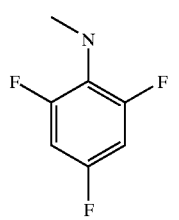 | N-{2-[2-(4-Amidinophenyl)-ethyl]-1-methyl-benzimidazol-5-yl}-N-methyl-2-[4-(2-amidinophenylamino)-piperid-1-yl]-acetamide, dihydrochloride |
| 41 | —CH₃ | 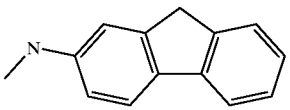 | N-{2-[2-(4-Amidinophenyl)-ethyl]-1-methyl-benzimidazol-5-yl}-N-methyl-2-[4-(2,4,6-trifluorophenylamino)-piperid-1-yl]-acetamide, dihydrochloride |
| 42 | —CH₃ | 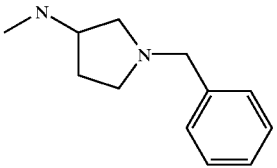 | N-{2-[2-(4-Amidinophenyl)-ethyl]-1-methyl-benzimidazol-5-yl}-N-methyl-2-[4-(aminofluorene)-piperid-1-yl]-acetamide, dihydrochloride |
| 43 | —CH₃ | 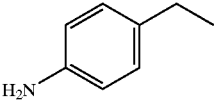 | N-{2-[2-(4-Amidinophenyl)-ethyl]-1-methyl-benzimidazol-5-yl}-N-methyl-2-{4-[(N-benzyl)-2-pyrrolidylamino]-piperid-1-yl}-acetamide, dihydrochloride |
| 44 | 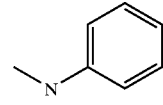 | 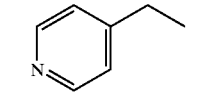 | N-{2-[2-(4-Amidinophenyl)-ethyl]-1-methyl-benzimidazol-5-yl}-N-[4-aminophenyl-methyl]-2-(4-phenylamino-piperid-1-yl)-acetamide, dihydrochloride |
| 45 | 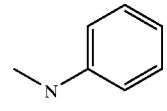 | 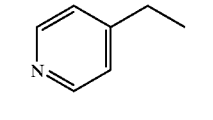 | N-{2-[2-(4-Amidinophenyl)-ethyl]-1-methyl-benzimidazol-5-yl}-N-[4-pyridylmethyl]-2-(4-phenylamino-piperid-1-yl)-acetamide, dihydrochloride |
| 46 | 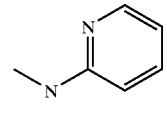 | | N-{2-[2-(4-Amidinophenyl)-ethyl]-1-methyl-benzimidazol-5-yl}-N-[4-pyridylmethyl]-2-[4-(2-pyridylamino)-piperid-1-yl]-acetamide, dihydrochloride |

TABLE 1-continued

[Structure shown at top of table:]
R⁵A—[piperidine]—N—CH₂—C(=O)—N(R³)—[1-methyl-benzimidazol-5-yl]—CH₂CH₂—[phenyl]—C(=NH)NH₂

| No | —R³ | —AR⁵ | Chemical name |
|---|---|---|---|
| 47 | 4-pyridylethyl | N-methyl-(2-chlorophenyl)amino | N-{2-[2-(4-Amidinophenyl)-ethyl]-1-methyl-benzimidazol-5-yl}-N-[4-pyridylmethyl]-2-[4-(2-chlorophenylamino)-piperid-1-yl]-acetamide, dihydrochloride |
| 48 | 4-pyridylethyl | N-methyl-(2-bromophenyl)amino | N-{2-[2-(4-Amidinophenyl)-ethyl]-1-methyl-benzimidazol-5-yl}-N-[4-pyridylmethyl]-2-[4-(2-bromophenylamino)-piperid-1-yl]-acetamide, dihydrochloride |
| 49 | 4-pyridylethyl | N-methyl-(2-fluorophenyl)amino | N-{2-[2-(4-Amidinophenyl)-ethyl]-1-methyl-benzimidazol-5-yl}-N-[4-pyridylmethyl]-2-[4-(2-fluorophenylamino)-piperid-1-yl]-acetamide, dihydrochloride |
| 50 | 3-nitrophenylethyl | N-methyl-(2-pyridyl)amino | N-{2-[2-(4-Amidinophenyl)-ethyl]-1-methyl-benzimidazol-5-yl}-N-[3-nitrophenylmethyl]-2-[4-(2-pyridylamino)-piperid-1-yl]-acetamide, dihydrochloride |
| 51 | 4-dimethylamino-naphth-1-ylethyl | N-methyl-(2-pyridyl)amino | N-{2-[2-(4-Amidinophenyl)-ethyl]-1-methyl-benzimidazol-5-yl}-N-[4-dimethylamino-naphth-1-ylmethyl]-2-[4-(2-pyridylamino)-piperid-1-yl]-acetamide, dihydrochloride |
| 52 | H | N-methyl-(2-pyridyl)amino | N-{2-[2-(4-Amidinophenyl)-ethyl]-1-methyl-benzimidazol-5-yl}-2-[4-(2-pyridylamino)-piperid-1-yl]-acetamide, dihydrochloride |
| 53 | ethyl ethanecarboxylate | N-methyl-(2-pyridyl)amino | N-{2-[2-(4-Amidinophenyl)-ethyl]-1-methyl-benzimidazol-5-yl}-N-[ethyl ethanecarboxylate]-2-[4-(2-pyridylamino)-piperid-1-yl]-acetamide, dihydrochloride |
| 54 | ethanecarboxylic acid | N-methyl-(2-pyridyl)amino | N-{2-[2-(4-Amidinophenyl)-ethyl]-1-methyl-benzimidazol-5-yl}-N-[ethanecarboxylic acid]-2-[4-(2-pyridylamino)-piperid-1-yl]-acetamide, dihydrochloride |

TABLE 1-continued

| No | —R³ | —AR⁵ | Chemical name |
|---|---|---|---|
| 55 | 3-aminophenylmethyl | 2-pyridyl(N-methyl) | N-{2-[2-(4-Amidinophenyl)-ethyl]-1-methyl-benzimidazol-5-yl}-N-[3-aminophenyl-methyl]-2-[4-(2-pyridylamino)-piperid-1-yl]-acetamide, dihydrochloride |
| 56 | (1-methyl-1-phenyl)ethane | phenyl(N-methyl) | N-{2-[2-(4-Amidinophenyl)-ethyl]-1-methyl-benzimidazol-5-yl}-N-[(1-methyl-1-phenyl)-ethane]-2-[4-(phenylamino)-piperid-1-yl]-acetamide, dihydrochloride |
| 57 | benzyl | 2-pyridyl(N-methyl) | N-{2-[2-(4-Amidinophenyl)-ethyl]-1-methyl-benzimidazol-5-yl}-N-[benzyl]-2-[4-(2-pyridylamino)-piperid-1-yl]-acetamide, dihydrochloride |
| 58 | benzyl | 2-chlorophenyl(N-methyl) | N-{2-[2-(4-Amidinophenyl)-ethyl]-1-methyl-benzimidazol-5-yl}-N-benzyl-2-[4-(2-chlorophenylamino)-piperid-1-yl]-acetamide, dihydrochloride |
| 59 | benzyl | 2-fluorophenyl(N-methyl) | N-{2-[2-(4-Amidinophenyl)-ethyl]-1-methyl-benzimidazol-5-yl}-N-benzyl-2-[4-(2-fluorophenylamino)-piperid-1-yl]-acetamide, dihydrochloride |
| 60 | naphth-1-ylmethyl | 2-pyridyloxy(methoxy) | N-{2-[2-(4-Amidinophenyl)-ethyl]-1-methyl-benzimidazol-5-yl}-N-[naphth-1-ylmethyl]-2-[4-(2-pyridyloxy)-piperid-1-yl]-acetamide, dihydrochloride |
| 61 | CH₃ | 2-chloro-4-methylphenyl(N-methyl) | N-{2-[2-(4-Amidinophenyl)-ethyl]-1-methyl-benzimidazol-5-yl}-N-methyl-2-[4-(2-chloro-4-methylamino)-piperid-1-yl]-acetamide, dihydrochloride |
| 62 | CH₃ | 2-chloro-4-bromophenyl(N-methyl) | N-{2-[2-(4-Amidinophenyl)-ethyl]-1-methyl-benzimidazol-5-yl}-N-methyl-2-[4-(2-chloro-4-bromoamino)-piperid-1-yl]-acetamide, dihydrochloride |
| 63 | CH₃ | 2-methylphenyl(N-methyl) | N-{2-[2-(4-Amidinophenyl)-ethyl]-1-methyl-benzimidazol-5-yl}-N-methyl-2-[4-(2-methylamino)-piperid-1-yl]-acetamide, dihydrochloride |

TABLE 1-continued

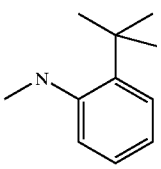

| No | —R³ | —AR⁵ | Chemical name |
|---|---|---|---|
| 64 | CH₃ | 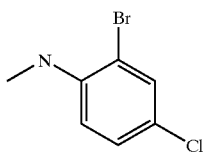 | N-{2-[2-(4-Amidinophenyl)-ethyl]-1-methyl-benzimidazol-5-yl}-N-methyl-2-[4-(2-tert.butylamino)-piperid-1-yl]-acetamide, dihydrochloride |
| 65 | CH₃ | 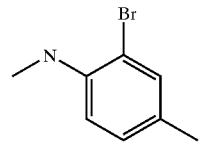 | N-{2-[2-(4-Amidinophenyl)-ethyl]-1-methyl-benzimidazol-5-yl}-N-methyl-2-[4-(2-bromo-4-chloroamino)-piperid-1-yl]-acetamide, dihydrochloride |
| 66 | CH₃ | 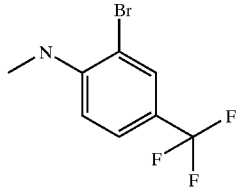 | N-{2-[2-(4-Amidinophenyl)-ethyl]-1-methyl-benzimidazol-5-yl}-N-methyl-2-[4-(2-bromo-4-methylamino)-piperid-1-yl]-acetamide, dihydrochloride |
| 67 | CH₃ | 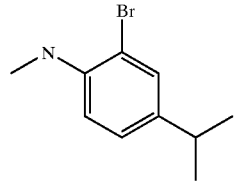 | N-{2-[2-(4-Amidinophenyl)-ethyl]-1-methyl-benzimidazol-5-yl}-N-methyl-2-[4-(2-bromo-4-trifluoromethylamino)-piperid-1-yl]-acetamide, dihydrochloride |
| 68 | CH₃ | 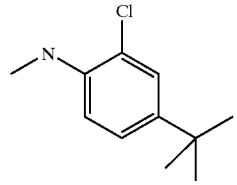 | N-{2-[2-(4-Amidinophenyl)-ethyl]-1-methyl-benzimidazol-5-yl}-N-methyl-2-[4-(2-bromo-4-isopropylamino)-piperid-1-yl]-acetamide, dihydrochloride |
| 69 | CH₃ | 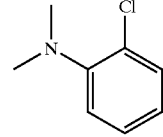 | N-{2-[2-(4-Amidinophenyl)-ethyl]-1-methyl-benzimidazol-5-yl}-N-methyl-2-[4-(2-chloro-4-tert.butylamino)-piperid-1-yl]-acetamide, dihydrochloride |
| 70 | CH₃ | | N-{2-[2-(4-Amidinophenyl)-ethyl]-1-methyl-benzimidazol-5-yl}-N-methyl-2-[4-(2-chloro-N-methylamino)-piperid-1-yl]-acetamide, dihydrochloride |

TABLE 1-continued

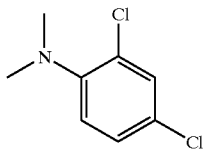

| No | —R³ | —AR⁵ | Chemical name |
|---|---|---|---|
| 71 | CH₃ | (2,4-dichloro-N,N-dimethylaminophenyl) | N-{2-[2-(4-Amidinophenyl)-ethyl]-1-methyl-benzimidazol-5-yl}-N-methyl-2-[4-(2,4-dichloro-N-methylamino)-piperid-1-yl]-acetamide, dihydrochloride |

TABLE 2

| No | —R³ | —AR⁵ | Chemical name |
|---|---|---|---|
| 72 | naphth-1-ylmethyl | N-methylanilino | N-{2-[2-(4-Amidinophenyl)-ethyl]-1-methyl-benzimidazol-5-yl}-N-[naphth-1-ylmethyl]-N'-phenyl-urea, hydrochloride |
| 73 | naphth-1-ylmethyl | 3-methoxy-N-methylanilino | N-{2-[2-(4-Amidinophenyl)-ethyl]-1-methyl-benzimidazol-5-yl}-N-[naphth-1-ylmethyl]-N'-(3-methoxy)-phenyl, hydrochloride |
| 74 | naphth-1-ylmethyl | 3-chloro-N-methylanilino | N-{2-[2-(4-Amidinophenyl)-ethyl]-1-methyl-benzimidazol-5-yl}-N-[naphth-1-ylmethyl]-N'-(3-chloro)-phenyl, hydrochloride |
| 75 | naphth-1-ylmethyl | 1-(N-methyl)naphthyl | N-{2-[2-(4-Amidinophenyl)-ethyl]-1-methyl-benzimidazol-5-yl}-N-[naphth-1-ylmethyl]-N'-(1-naphthyl)-urea, hydrochloride |
| 76 | naphth-1-ylmethyl | 4-(2-pyridyl)amino-cyclohexyl-N-methyl | N-{2-[2-(4-Amidinophenyl)-ethyl]-1-methyl-benzimidazol-5-yl}-N-[naphth-1-ylmethyl]-N'-[4-(2-pyridyl)-amino-cyclohexyl]-urea, hydrochloride |

TABLE 2-continued

[Structure: benzimidazole core with N-CH3, 2-[2-(4-amidinophenyl)ethyl] substituent, and 5-position N(R3)-C(=O)-R5A amide]

| No | —R³ | —AR⁵ | Chemical name |
|---|---|---|---|
| 77 | [1-ethyl-naphthalen-8-yl (naphth-1-ylmethyl)] | [1-benzyl-piperidin-4-yl-amino] | N-{2-[2-(4-Amidinophenyl)-ethyl]-1-methyl-benzimidazol-5-yl}-N-[naphth-1-ylmethyl]-N'-[4-(benzyl)-piperidin-4-yl]-urea, hydrochloride |
| 78 | [naphth-1-ylmethyl] | [3-(dimethylamino)propyl-N-methyl] | N-{2-[2-(4-Amidinophenyl)-ethyl]-1-methyl-benzimidazol-5-yl}-N-[naphth-1-ylmethyl]-N'-methyl-N'-(3-dimethylaminopropyl)-urea, hydrochloride |
| 79 | [naphth-1-ylmethyl] | [1-methyl-4-(2-pyridylamino)-piperidin-4-yl] | N-{2-[2-(4-Amidinophenyl)-ethyl]-1-methyl-benzimidazol-5-yl}-N-[naphth-1-ylmethyl]-N'-[4-(2-pyridyl)-amino]-piperid-1-ine-urea, hydrochloride |
| 80 | —CH₃ | [N-methyl-N-(naphth-2-ylmethyl)amino] | N-{2-[2-(4-Amidinophenyl)-ethyl]-1-methyl-benzimidazol-5-yl}-N-[naphth-1-ylmethyl]-N'-[4-(2-naphthylmethylamino)]-urea, hydrochloride |
| 81 | H | [3-(dimethylamino)propyl-N-methyl] | N-{2-[2-(4-Amidinophenyl)-ethyl]-1-methyl-benzimidazol-5-yl}-N'-methyl-N'-(3-dimethylaminopropyl)-urea, hydrochloride |
| 82 | H | [1-methyl-4-(2-pyridylamino)-piperidin-4-yl] | N-{2-[2-(4-Amidinophenyl)-ethyl]-1-methyl-benzimidazol-5-yl}-N'-[4-(2-pyridyl)-amino]-piperid-1-ine urea, hydrochloride |

TABLE 3

[Structure: R5A-piperidin-4-yl-N-CH2-CH2-N(R3)- attached to 5-position of 1-methyl-benzimidazole with 2-[2-(4-amidinophenyl)ethyl] group]

| No | —R³ | —AR⁵ | Chemical name |
|---|---|---|---|
| 83 | [1-ethyl-naphthyl (naphth-1-ylmethyl)] | [2-pyridylamino] | N-{2-[2-(4-Amidinophenyl)-ethyl]-1-methyl-benzimidazol-5-yl}-N-[naphth-1-ylmethyl]-2-[4-(2-pyridylamino)-piperid-1-yl]-ethylamine, dihydrochloride |

EXAMPLE 84

N-{2-[2-(4-Aminobenzyl)-ethyl]-1-methyl-benzimidazol-5-yl}-N-methyl-2-[4-(2-chloro-4-fluorophenylamino)-piperid-1-yl]-acetamide, Ditrifluoroacetate

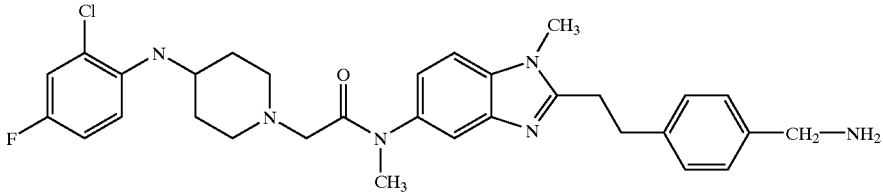

Step a) 2-[2-(4-Aminobenzyl)-ethyl]-1-methyl-5-methylamino-benzimidazole

2-[2-(4-cyanophenyl)-ethyl]-1-methyl-5-methylamino-benzimidazole (4.9 g, 17 mmol) synthesised According to Example 4 step b is hydrogenated in 100 mL of methanol and 25 mL of tetrahydrofuran in the presence of 1 g of Raney nickel and 4 mL of saturated alcoholic ammonia solution at ambient temperature and normal pressure for 10 hours. Then the solution is shaken for another 2 hours at 30-40° C. and 5 bar. It is distilled off from the mother liquor and the residue is chromatographed on silica gel.

Yield: 3.4 g (69%).

Step b) 2-[2-(4-(tert-butyloxycarbonylamino)benzyl)-ethyl]-1-methyl-5-methylamino-benzimidazole 2-[2-(4-Aminobenzyl)-ethyl]-1-methyl-5-methylamino-benzimidazole (3.4 g, 11.6 mmol) are dissolved in 50 mL of dichloromethane and cooled to 5° C. Within 30 min a solution of 2.5 g (11.5 mmol) of di-tert-butyldicarbonate in 10 mL of dichloromethane is added dropwise thereto. The mixture is stirred for 2 hours at about 5° C. and then for 2 hours at ambient temperature. The compounds were purified by column chromatography on silica gel.

Yield: 3.0 g (66%).

Step c) N-{2-[2-(4-(tert-butyloxycarbonylamino)benzyl)-ethyl]-1-methyl-benzimidazol-5-yl}-N-methyl-2-chloroacetamide According to Example 1, step e, 2-[2-(4-(tert-butyloxycarbonylamino)benzyl)-ethyl]-1-methyl-5-methylamino-benzimidazole (2.1 g, 5.3 mmol) was reacted with chloroacetylchloride. The product was purified by chromatography on silica gel.

Yield: 2.5 g (100%).

Step d) N-{2-[2-(4-(Aminobenzyl)-ethyl]-1-methyl-benzimidazol-5-yl}-N-methyl-2-[4-(2-chloro-4-fluorophenylamino)-piperid-1-yl] acetamide, Ditrifluoroacetate 1.2 g (3.5 mmol) of 4-(2-chloro-4-fluorophenylamino)-1-piperidine were alkylated with 1.3 g (2.7 mmol) of N-{2-[2-(4-(tert-butyloxycarbonylamino)benzyl)-ethyl]-1-methyl-benzimidazol-5-yl}-N-methyl-2-chloroacetamide and 2.8 g potassium carbonate in 15 mL of dimethylformamide within 3 hours at 80-90° C. Then the protecting group was cleaved with trifluoroacetic acid. The title compound was purified by column chromatography on silica gel.

Yield: 1.5 g (84%).

$^1$H-NMR (250 MHz, CD$_3$OD): δ=7.95-6.61 (m, 10H, aryl-H), 4.09 (s, 2H, ph-CH$_2$—N), 3.94-3.50 and 3.18-2.93 (m, 5H, piperidine), 3.82 (s, 3H, imidazol-CH$_3$), 3.42 (t, 2H, J=6.7 Hz, CH$_2$-ph), 3.38 (s, 3H, N—CH$_3$), 3.23 (t, 2H, J=8.2 Hz, CH$_2$-ph), 2.41-2.07 (m, 2H, CH$_2$-piperidine), 1.97-1.68 (m, 2H, CH$_2$-piperidine).

The following Table 4 lists other compounds of general formula (I) synthesised according to the invention analogously to Example 84 described hereinbefore.

TABLE 4

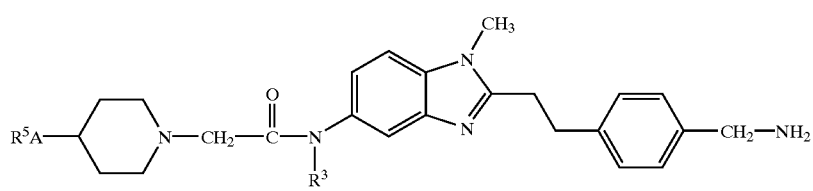

| No | —R$^3$ | —AR$^5$ | Chemical name |
|---|---|---|---|
| 85 | naphth-1-ylmethyl | 2-pyridyl (N-methyl) | N-{2-[2-(4-Aminomethylphenyl)-ethyl]-1-methyl-benzimidazol-5-yl}-N-[naphth-1-ylmethyl]-2-[4-(2-pyridylamino)-piperid-1-yl]-acetamide, dihydrochloride |

TABLE 4-continued

| No | —R³ | —AR⁵ | Chemical name |
|---|---|---|---|
| 86 | naphth-1-ylmethyl | benzyl | N-{2-[2-(4-Aminomethylphenyl)-ethyl]-1-methyl-benzimidazol-5-yl}-N-[naphth-1-ylmethyl]-2-[4-(benzyl)-piperid-1-yl]-acetamide, dihydrochloride |
| 87 | naphth-1-ylmethyl | 4-chlorophenyl-N-methyl | N-{2-[2-(4-Aminomethylphenyl)-ethyl]-1-methyl-benzimidazol-5-yl}-N-[naphth-1-ylmethyl]-2-[4-(4-chlorophenylamino)-piperid-1-yl]-acetamide, dihydrochloride |
| 88 | naphth-1-ylmethyl | 3-chlorophenyl-N-methyl | N-{2-[2-(4-Aminomethylphenyl)-ethyl]-1-methyl-benzimidazol-5-yl}-N-[naphth-1-ylmethyl]-2-[4-(3-chlorophenylamino)-piperid-1-yl]-acetamide, dihydrochloride |
| 89 | naphth-1-ylmethyl | 2-chlorophenyl-N-methyl | N-{2-[2-(4-Aminomethylphenyl)-ethyl]-1-methyl-benzimidazol-5-yl}-N-[naphth-1-ylmethyl]-2-[4-(2-chlorophenylamino)-piperid-1-yl]-acetamide, dihydrochloride |
| 90 | naphth-1-ylmethyl | 2-pyridyl-N-methyl | N-{2-[2-(4-Aminomethylphenyl)-ethyl]-1-methyl-benzimidazol-5-yl}-N-[naphth-1-ylmethyl]-2-[4-(2-pyridyl-N-methyl-amino)-piperid-1-yl]-acetamide, dihydrochloride |
| 91 | naphth-1-ylmethyl | 2-naphthyl-N-methyl | N-{2-[2-(4-Aminomethylphenyl)-ethyl]-1-methyl-benzimidazol-5-yl}-N-[naphth-1-ylmethyl]-2-[4-(2-naphthylamino)-piperid-1-yl]-acetamide, dihydrochloride |
| 92 | naphth-1-ylmethyl | 4-biphenyl-N-methyl | N-{2-[2-(4-Aminomethylphenyl)-ethyl]-1-methyl-benzimidazol-5-yl}-N-[naphth-1-ylmethyl]-2-[4-(4-biphenylamino)-piperid-1-yl]-acetamide, dihydrochloride |

TABLE 4-continued

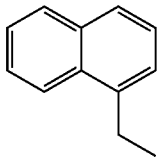

| No | —R³ | —AR⁵ | Chemical name |
|---|---|---|---|
| 93 | 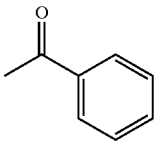 | 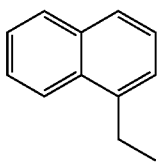 | N-{2-[2-(4-Aminomethylphenyl)-ethyl]-1-methyl-benzimidazol-5-yl}-N-[naphth-1-ylmethyl]-2-[4-(phenylcarbonyl)-piperid-1-yl]-acetamide, dihydrochloride |
| 94 | 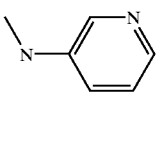 | 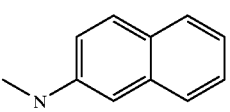 | N-{2-[2-(4-Aminomethylphenyl)-ethyl]-1-methyl-benzimidazol-5-yl}-N-[naphth-1-ylmethyl]-2-[4-(3-pyridylamino)-piperid-1-yl]-acetamide, dihydrochloride |
| 95 | —CH₃ | 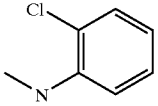 | N-{2-[2-(4-Aminomethylphenyl)-ethyl]-1-methyl-benzimidazol-5-yl}-N-methyl-2-[4-(2-naphthylamino)-piperid-1-yl]-acetamide, dihydrochloride |
| 96 | —CH₃ | 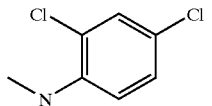 | N-{2-[2-(4-Aminomethylphenyl)-ethyl]-1-methyl-benzimidazol-5-yl}-N-methyl-2-[4-(2-chlorophenylamino)-piperid-1-yl]-acetamide, dihydrochloride |
| 97 | —CH₃ | 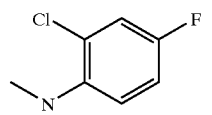 | N-{2-[2-(4-Aminomethylphenyl)-ethyl]-1-methyl-benzimidazol-5-yl}-N-methyl-2-[4-(2,4-dichlorophenylamino)-piperid-1-yl]-acetamide, dihydrochloride |
| 98 | —CH₃ | 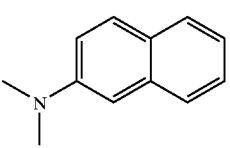 | N-{2-[2-(4-Aminomethylphenyl)-ethyl]-1-methyl-benzimidazol-5-yl}-N-methyl-2-[4-(2-chloro-4-fluorophenylamino)-piperid-1-yl]-acetamide, dihydrochloride |
| 99 | —CH₃ | 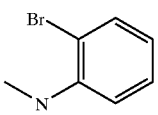 | N-{2-[2-(4-Aminomethylphenyl)-ethyl]-1-methyl-benzimidazol-5-yl}-N-methyl-2-[4-(2-naphthyl-N-methylamino)-piperid-1-yl]-acetamide, dihydrochloride |
| 100 | —CH₃ | 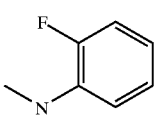 | N-{2-[2-(4-Aminomethylphenyl)-ethyl]-1-methyl-benzimidazol-5-yl}-N-methyl-2-[4-(2-bromophenylamino)-piperid-1-yl]-acetamide, dihydrochloride |
| 101 | —CH₃ | | N-{2-[2-(4-Aminomethylphenyl)-ethyl]-1-methyl-benzimidazol-5-yl}-N-methyl-2-[4-(2-fluorophenylamino)-piperid-1-yl]-acetamide, dihydrochloride |

TABLE 4-continued

R⁵A—[piperidine]—N—CH₂—C(=O)—N(R³)—[1-methyl-benzimidazol-5-yl]—CH₂CH₂—[phenyl]—CH₂—NH₂

| No | —R³ | —AR⁵ | Chemical name |
|---|---|---|---|
| 102 | —CH₃ | N-methyl-2-iodoanilino | N-{2-[2-(4-Aminomethylphenyl)-ethyl]-1-methyl-benzimidazol-5-yl}-N-methyl-2-[4-(2-iodophenylamino)-piperid-1-yl]-acetamide, dihydrochloride |
| 103 | 4-aminobenzyl (H₂N-C₆H₄-CH₂-) | N-methyl-phenylamino | N-{2-[2-(4-Aminomethylphenyl)-ethyl]-1-methyl-benzimidazol-5-yl}-N-[4-aminophenyl-methyl]-2-(4-phenylamino-piperid-1-yl)-acetamide, dihydrochloride |
| 104 | 3-nitrobenzyl (O₂N-C₆H₄-CH₂-) | N-methyl-2-pyridylamino | N-{2-[2-(4-Aminomethylphenyl)-ethyl]-1-methyl-benzimidazol-5-yl}-N-[3-nitrophenylmethyl]-2-[4-(2-pyridylamino)-piperide-1-yl]-acetamide, dihydrochloride |

The following Table 4 lists other compounds of general formula (I) synthesised according to the invention analogously to the Examples described hereinbefore.

TABLE 5

R⁵A—[piperidine]—N—CH₂—C(=O)—N(CH₃)—[1-methyl-benzimidazol-5-yl]—CH₂CH₂—[phenyl]—C(=NH)—NH₂

| No | —AR⁵ | Chemical name |
|---|---|---|
| 105 | N-methyl-4-chloroanilino | N-{2-[2-(4-Amidinophenyl)-ethyl]-1-methyl-benzimidazol-5-yl}-N-methyl-2-[4-(4-chlorophenylamino)-piperid-1-yl]-acetamide, dihydrochloride |
| 106 | N-methyl-3-chloroanilino | N-{2-[2-(4-Amidinophenyl)-ethyl]-1-methyl-benzimidazol-5-yl}-N-methyl-2-[4-(3-chlorophenylamino)-piperid-1-yl]-acetamide, dihydrochloride |
| 107 | N-methyl-3,4-dichloroanilino | N-{2-[2-(4-Amidinophenyl)-ethyl]-1-methyl-benzimidazol-5-yl}-N-methyl-2-[4-(3,4-dichlorophenylamino)-piperid-1-yl]-acetamide, dihydrochloride |

TABLE 5-continued

| No | —AR⁵ | Chemical name |
|---|---|---|
| 108 | (phenyl-N(CH₃)-) | N-{2-[2-(4-Amidinophenyl)-ethyl]-1-methyl-benzimidazol-5-yl}-N-methyl-2-[4-(phenylamino)-piperid-1-yl]-acetamide, dihydrochloride |

The compounds according to the invention are characterised by their tryptase-inhibiting activity. This ability to inhibit tryptase was investigated using the test described below.

The measurement is carried out in Tris HCl buffer (100 mM), which additionally contains calcium (5 mM) and heparin (100 mg/ml), at pH 7.4. The standard used is rh beta tryptase which may be obtained commercially from Promega, for example. The substrate used is N-p-tosyl-Gly-Pro-Lys-para-nitroaniline in a concentration of 0.6 mM. The substrate is digested with tryptase to form p-nitroaniline which can be measured at 405 nm. Usually, an incubation period of 5 minutes and an incubation temperature of 37° C. are chosen. The enzyme activity used is 0.91 U/ml. The measurements are carried out in an Autoanalyser (Cobas Bio) made by Hofmann LaRoche. The potential inhibitory substances are used in concentrations of 10 μM in the screening, the inhibition of the tryptase being given in percent. The $IC_{50}$ is determined at over 70% inhibition (concentration at which 50% of the enzyme activity is inhibited). After 5 minutes' pre-incubation of the potential inhibitory substances, the substrate is added to start the reaction, the formation of p-nitroaniline being taken as a measurement of the enzyme activity after 5 minutes, after testing the linearity.

Table 6 which follows shows the results obtained in the in vitro test; the symbols have the following meaning:

TABLE 6

| Example | Tryptase-inhibiting activity |
|---|---|
| 1 | ++ |
| 2 | ++ |
| 3 | ++ |
| 4 | +++ |
| 5 | + |
| 6 | +++ |
| 7 | ++ |
| 8 | ++ |
| 9 | ++ |
| 10 | +++ |
| 11 | +++ |
| 12 | +++ |
| 13 | ++ |
| 14 | ++ |
| 15 | ++ |
| 16 | ++ |
| 17 | ++ |
| 18 | ++ |
| 19 | ++ |
| 20 | ++ |
| 21 | ++ |
| 22 | +++ |
| 23 | ++ |
| 24 | +++ |
| 25 | + |
| 26 | +++ |
| 27 | ++ |
| 28 | ++ |
| 29 | + |
| 30 | +++ |
| 31 | +++ |
| 32 | +++ |
| 33 | +++ |
| 34 | ++ |
| 35 | +++ |
| 36 | +++ |
| 37 | +++ |
| 38 | ++ |
| 39 | ++ |
| 40 | + |
| 42 | ++ |
| 43 | ++ |
| 44 | ++ |
| 45 | ++ |
| 46 | ++ |
| 50 | ++ |
| 51 | ++ |
| 52 | + |
| 53 | ++ |
| 54 | ++ |
| 55 | ++ |
| 57 | ++ |
| 58 | +++ |
| 59 | +++ |
| 60 | ++ |
| 61 | +++ |
| 62 | +++ |
| 63 | ++ |
| 64 | ++ |
| 65 | +++ |
| 66 | +++ |
| 67 | ++ |
| 68 | + |
| 69 | + |
| 72 | + |
| 73 | + |
| 74 | + |
| 75 | ++ |
| 76 | + |
| 77 | ++ |
| 78 | + |
| 79 | + |

TABLE 6-continued

| Example | Tryptase-inhibiting activity |
|---------|------------------------------|
| 80      | +    |
| 81      | +    |
| 82      | +    |
| 84      | ++   |
| 105     | +++  |
| 106     | +++  |
| 107     | +++  |
| 108     | ++   |

+++ IC50: 0.0005–0.0030 µM,
++: IC50: 0.0040–0.0300 µM
+: IC50: 0.0310–1.0000 µM

The tryptase inhibitors according to the invention may be administered orally, transdermally, by inhalation or parenterally. The compounds according to the invention occur as active ingredients in conventional preparations, for example in compositions which consist essentially of an inert pharmaceutical carrier and an effective dose of the active substance, such as for example tablets, coated tablets, capsules, powders, solutions, suspensions, emulsions, syrups, suppositories, transdermal system etc. An effective dose of the compounds according to the invention is between 1 and 100, preferably between 1 and 50, most preferably between 5-30 mg/dose for oral administration, and between 0.001 and 50, preferably between 0.1 and 10 dose for intravenous or intramuscular administration. For inhalation, according to the invention, solutions containing 0.01 to 1.0, preferably 0.1 to 0.5% active are suitable. For administration by inhalation the use of powders is preferred. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmacologically active substances. Suitable preparations include for example tablets, capsules, suppositories, solutions, elixirs, emulsions or dispersible powders. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dose is between 1 and 800 mg, preferably 10-300 mg per adult.

The Examples which follow illustrate the present invention without restricting its scope:

EXAMPLES OF PHARMACEUTICAL FORMULATIONS

| A) | Tablets | per tablet |
|----|---------|------------|
|    | active substance | 100 mg |
|    | lactose | 140 mg |
|    | corn starch | 240 mg |
|    | polyvinylpyrrolidone | 15 mg |
|    | magnesium stearate | 5 mg |
|    |         | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|----|---------|------------|
|    | active substance | 80 mg |
|    | corn starch | 190 mg |
|    | lactose | 55 mg |
|    | microcrystalline cellulose | 35 mg |
|    | polyvinylpyrrolidone | 15 mg |
|    | sodium-carboxymethyl starch | 23 mg |
|    | magnesium stearate | 2 mg |
|    |         | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) | Coated tablets | per coated tablet |
|----|----------------|-------------------|
|    | Active substance | 5 mg |
|    | Corn starch | 41.5 mg |
|    | Lactose | 30 mg |
|    | Polyvinylpyrrolidone | 3 mg |
|    | Magnesium stearate | 0.5 mg |
|    |                | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) | Capsules | per capsule |
|---|---|---|
| | Active substance | 50 mg |
| | Corn starch | 268.5 mg |
| | Magnesium stearate | 1.5 mg |
| | | 320 mg |

The substance and corn starch are mixed and moistened with water. The moist mass is screened and dried. The dry granules are screened and mixed with magnesium stearate. The finished mixture is packed into size 1 hard gelatine capsules.

| E) | Ampoule solution | |
|---|---|---|
| | active substance | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) | Suppositories | |
|---|---|---|
| | Active substance | 50 mg |
| | Solid fat | 1650 mg |
| | | 1700 mg |

The solid fat is melted. The ground active substance is homogeneously dispersed at 40° C. It is cooled to 38° C. and poured into slightly chilled suppository moulds.

What is claimed is:

1. A compound of the formula (IA)

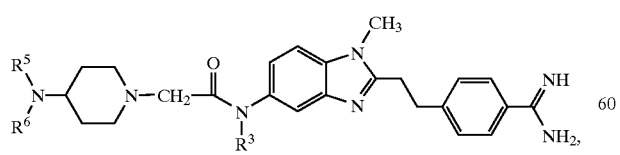

(IA)

wherein
$R^3$ denotes hydrogen, methyl, butyl, —$CH_2$—COOH, —$CH_2$—COO-ethyl, benzyl, pyridylmethyl or naphthylmethyl, wherein the aromatic and heteroaromatic groups may be substituted in each case by $C_1$-$C_6$-alkyl, —$NO_2$, —$NH_2$, —NH—$C_1$-$C_4$-alkyl, or —N($C_1$-$C_4$-alkyl)$_2$;

$R^5$ denotes a $C_1$-$C_4$-alkyl, $C_1$-$C_4$-alkanoyl, phenyl, pyridyl, benzoyl or pyridylcarbonyl group, while these groups may each optionally be substituted by one or more groups selected from among halogen, —OH, —$C_1$-$C_4$-alkyl, $C_1$-$C_4$-alkoxy, phenyl, naphthyl, phenoxy, benzyl, benzyloxy, —CO—O—$C_1$-$C_4$-alkyl, —$NO_2$, —$NH_2$, —NH—$C_1$-$C_4$-alkyl and —N($C_1$-$C_4$-alkyl)$_2$, and $R^6$ denotes a hydrogen atom or a methyl group, or their tautomers, racemates, enantiomers, diastereomers and mixtures thereof, or the pharmaceutically acceptable acid addition salts thereof.

2. The compound of formula IA according to claim 1, wherein
$R^5$ is pyrid-2-yl, pyrid-3-yl or a phenyl group each optionally substituted by one or two halogen atoms.

3. The compound of formula IA according to claim 1, wherein
$R^5$ is a phenyl group of formula

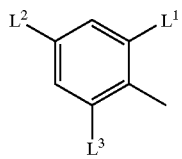

wherein
$L^1$ denotes a fluorine, chlorine, bromine or iodine atom, and
$L^2$ and $L^3$ independently of one another each denote a hydrogen, fluorine or chlorine atom.

4. A compound selected from:

N-{2-[2-(4-Amidinophenyl)-ethyl]-1-methyl-benzimidazol-5-yl}-N-[naphth-1-ylmethyl]-2-(4-phenylamino-piperid-1-yl)-acetamide, N-{2-[2-(4-Amidinophenyl)-ethyl]-1-methyl-benzimidazol-5-yl}-N-[naphth-1-ylmethyl]-2-{4-[N-methyl-N-(3-hydroxypropyl)-amino]-piperid-1-yl}-acetamide, N-{2-[2-(4-Amidinophenyl)-ethyl]-1-methyl-benzimidazol-5-yl}-N-(4-tert-butylphenylmethyl)-2-[4-(2-pyridylamino)-piperid-1-yl]-acetamide, N-{2-[2-(4-Amidinophenyl)-ethyl]-1-methyl-benzimidazol-5-yl}-N-(methyl)-2-[4-(2-chlorophenylamino)-piperid-1-yl]-acetamide N-{2-[2-(4-Amidinophenyl)-ethyl]-1-methyl-benzimidazol-5-yl}-N-[naphth-1-ylmethyl]-2-[4-(2-pyridylamino)-piperid-1-yl]-acetamide, N-{2-[2-(4-Amidinophenyl)-ethyl]-1-methyl-benzimidazol-5-yl}-N-[naphth-1-ylmethyl]-2-[4-(2-pyridylcarboxylic acid amide)-piperid-1-yl]-acetamide, N-{2-[2-(4-Amidinophenyl)-ethyl]-1-methyl-benzimidazol-5-yl}-N-[naphth-1-ylmethyl]-2-[4-benzoic acid amide-piperid-1-yl]-acetamide, N-{2-[2-(4-Amidinophenyl)-ethyl]-1-methyl-benzimidazol-5-yl}-N-[naphth-1-ylmethyl]-2-[4-(4-chlorophenylamino)-piperid-1-yl]-acetamide, N-{2-[2-(4-Amidinophenyl)-ethyl]-1-methyl-benzimidazol-5-yl}-N-[naphth-1-ylmethyl]-2-[4-(3-chlorophenylamino)-piperid-1-yl]-acetamide, N-{2-[2-(4-Amidinophenyl)-ethyl]-1-methyl-benzimidazol-5-yl}-N-[naphth-1-ylmethyl]-2-[4-(2-chlorophenylamino)-piperid-1-yl]-acetamide, N-{2-[2-(4-Amidinophenyl)-ethyl]-1-methyl-benzimidazol-5-yl}-N-[naphth-1-ylmethyl]-2-[4-(4-dimethylaminophenyl-amino)-piperid-1-yl]-acetamide, N-{2-[2-(4-Amidinophenyl)-ethyl]-1-methyl-benzimidazol-5-yl}-N-[naphth-1-ylmethyl]-2-[4-(4-methoxyphenylamino)-piperid-1-yl]-acetamide, N-{2-[2-(4-Amidinophenyl)-ethyl]-1-methyl-benzimidazol-5-yl}-N-[naphth-1-ylmethyl]-2-[4-(4-benzyloxy-phenylamino)-piperid-1-yl]-acetamide, N-{2-[2-(4-Amidinophenyl)-ethyl]-1-methyl-benzimidazol-5-yl}-N-[naphth-1-ylmethyl]-2-[4-(4-hydroxyphenylamino)-piperid-1-yl]-acetamide, N-{2-[2-(4-Amidinophenyl)-ethyl]-1-methyl-benzimidazol-5-yl}-N-[naphth-1-ylmethyl]-2-[4-(2-pyridyl-N-methyl-amino)-piperid-1-yl]-acetamide, N-{2-[2-(4-Amidinophenyl)-ethyl]-1-methyl-benzimidazol-5-yl}-N-[naphth-1-ylmethyl]-2-[4-(ethyl N-methyl-N-propionate)-piperid-1-yl]-acetamide, N-{2-[2-(4-Amidinophenyl)-ethyl]-1-methyl-benzimidazol-5-yl}-N-[naphth-1-ylmethyl]-2-[4-(2-naphthylamino)-piperid-1-yl]-acetamide, N-{2-[2-(4-Amidinophenyl)-ethyl]-1-methyl-benzimidazol-5-yl}-N-[naphth-1-ylmethyl]-2-[4-(4-biphenylamino)-piperid-1-yl]-acetamide, N-{2-[2-(4-Amidinophenyl)-ethyl]-1-methyl-benzimidazol-5-yl}-N-[naphth-1-ylmethyl]-2-[4-(N-methyl-N-propionic acid)-piperid-1-yl]-acetamide, diacetate N-{2-[2-(4-Amidinophenyl)-ethyl]-1-methyl-benzimidazol-5-yl}-N-[naphth-1-ylmethyl]-2-[4-(3-pyridylamino)-piperid-1-yl]-acetamide, N-{2-[2-(4-Amidinophenyl)-ethyl]-1-methyl-benzimidazol-5-yl}-N-[naphth-1-ylmethyl]-2-[4-(4-pyridylamino)-piperid-1-yl]-acetamide, N-{2-[2-(4-Amidinophenyl)-ethyl]-1-methyl-benzimidazol-5-yl}-N-methyl-2-[4-(2-pyridylamino)-piperid-1-yl]-acetamide, N-{2-[2-(4-Amidinophenyl)-ethyl]-1-methyl-benzimidazol-5-yl}-N-methyl-2-[4-(2-pyridylmethylamino)-piperid-1-yl]-acetamide, N-{2-[2-(4-Amidinophenyl)-ethyl]-1-methyl-benzimidazol-5-yl}-N-methyl-2-[4-(2-naphthylamino)-piperid-1-yl]-acetamide, N-{2-[2-(4-Amidinophenyl)-ethyl]-1-methyl-benzimidazol-5-yl}-N-methyl-2-[4-(2-chlorophenylamino)-piperid-1-yl]-acetamide, N-{2-[2-(4-Amidinophenyl)-ethyl]-1-methyl-benzimidazol-5-yl}-N-methyl-2-[4-(2,4-dichlorophenylamino)-piperid-1-yl]-acetamide, N-{2-[2-(4-Amidinophenyl)-ethyl]-1-methyl-benzimidazol-5-yl}-N-methyl-2-[4-(2-chloro-4-fluorophenylamino)-piperid-1-yl]-acetamide, N-{2-[2-(4-Amidinophenyl)-ethyl]-1-methyl-benzimidazol-5-yl}-N-methyl-2-[4-(2-naphthyl-N-methylamino)-piperid-1-yl]-acetamide, N-{2-[2-(4-Amidinophenyl)-ethyl]-1-methyl-benzimidazol-5-yl}-N-methyl-2-[4-(2-bromophenylamino)-piperid-1-yl]-acetamide, N-{2-[2-(4-Amidinophenyl)-ethyl]-1-methyl-benzimidazol-5-yl}-N-methyl-2-[4-(2-fluorophenylamino)-piperid-1-yl]-acetamide, N-{2-[2-(4-Amidinophenyl)-ethyl]-1-methyl-benzimidazol-5-yl}-N-methyl-2-[4-(2-iodophenylamino)-piperid-1-yl]-acetamide, N-{2-[2-(4-Amidinophenyl)-ethyl]-1-methyl-benzimidazol-5-yl}-N-methyl-2-[4-(2-trifluoromethylphenylamino)-piperid-1-yl]-acetamide, N-{2-[2-(4-Amidinophenyl)-ethyl]-1-methyl-benzimidazol-5-yl}-N-methyl-2-[4-(2-trifluoromethoxyphenylamino)-piperid-1-yl]-acetamide, N-{2-[2-(4-Amidinophenyl)-ethyl]-1-methyl-benzimidazol-5-yl}-N-methyl-2-[4-(2-amidinophenylamino)-piperid-1-yl]-acetamide, N-{2-[2-(4-Amidinophenyl)-ethyl]-1-methyl-benzimidazol-5-yl}-N-methyl-2-[4-(2,4,6-trifluorophenylamino)-piperid-1-yl]-acetamide, N-{2-[2-(4-Amidinophenyl)-ethyl]-1-methyl-benzimidazol-5-yl}-N-[4-aminophenyl-methyl]-2-(4-phenylamino-piperid-1-yl)-acetamide, N-{2-[2-(4-Amidinophenyl)-ethyl]-1-methyl-benzimidazol-5-yl}-N-[4-pyridylmethyl]-2-(4-phenylamino-piperid-1-yl)-acetamide, N-{2-[2-(4-Amidinophenyl)-ethyl]-1-methyl-benzimidazol-5-yl}-N-[4-pyridylmethyl]-2-[4-(2-pyridylamino)-piperid-1-yl]-acetamide, N-{2-[2-(4-Amidinophenyl)-ethyl]-1-methyl-benzimidazol-5-yl}-N-[4-pyridylmethyl]-2-[4-(2-chlorophenylamino)-piperid-1-yl]-acetamide, N-{2-[2-(4-Amidinophenyl)-ethyl]-1-methyl-benzimidazol-5-yl}-N-[4-pyridylmethyl]-2-[4-(2-bromophenylamino)-piperid-1-yl]-acetamide, N-{2-[2-(4-Amidinophenyl)-ethyl]-1-methyl-benzimidazol-5-yl}-N-[4-pyridylmethyl]-2-[4-(2-fluorophenylamino)-piperid-1-yl]-acetamide, N-{2-[2-(4-Amidinophenyl)-ethyl]-1-methyl-benzimidazol-5-yl}-N-[3-nitrophenylmethyl]-2-[4-(2-pyridylamino)-piperid-1-yl]-acetamide, N-{2-[2-(4-Amidinophenyl)-ethyl]-1-methyl-benzimidazol-5-yl}-N-[4-dimethylamino-naphth-1-ylmethyl]-2-[4-(2-pyridylamino)-piperid-1-yl]-acetamide, N-{2-[2-(4-Amidinophenyl)-ethyl]-1-methyl-benzimidazol-5-yl}-2-[4-(2-pyridylamino)-piperid-1-yl]-acetamide, N-{2-[2-(4-Amidinophenyl)-ethyl]-1-methyl-benzimidazol-5-yl}-N-[ethyl ethanecarboxylate]-2-[4-(2-pyridylamino)-piperid-1-yl]-acetamide, N-{2-[2-(4-Amidinophenyl)-ethyl]-1-methyl-benzimidazol-5-yl}-N-[ethanecarboxylic acid]-2-[4-(2-pyridylamino)-piperid-1-yl]-acetamide, N-{2-[2-(4-Amidinophenyl)-ethyl]-1-methyl-benzimidazol-5-yl}-N-[3-aminophenyl-methyl]-2-[4-(2-pyridylamino)-piperid-1-yl]-acetamide, N-{2-[2-(4-Amidinophenyl)-ethyl]-1-methyl-benzimidazol-5-yl}-N-[(1-methyl-1-phenyl)-ethane]-2-[4-(phenylamino)-piperid-1-yl]-acetamide, N-{2-[2-(4-Amidinophenyl)-ethyl]-1-methyl-benzimidazol-5-yl}-N-[benzyl]-2-[4-(2-pyridylamino)-piperid-1-yl]-acetamide, N-{2-[2-(4-Amidinophenyl)-ethyl]-1-methyl-benzimidazol-5-yl}-N-benzyl-2-[4-(2-chlorophenylamino)-piperid-1-yl]-acetamide, N-{2-[2-(4-Amidinophenyl)-ethyl]-1-methyl-benzimidazol-5-yl}-N-benzyl-2-[4-(2-fluorophenylamino)-piperid-1-yl]-acetamide, N-{2-[2-(4-Amidinophenyl)-ethyl]-1-methyl-benzimidazol-5-yl}-N-methyl-2-[4-(2-chloro-4-methylamino)-piperid-1-yl]-acetamide, N-{2-[2-(4-Amidinophenyl)-ethyl]-1-methyl-benzimidazol-5-yl}-N-methyl-2-[4-(2-chloro-4-bromoamino)-piperid-1-yl]-acetamide, N-{2-[2-(4-Amidinophenyl)-ethyl]-1-methyl-benzimidazol-5-yl}-N-methyl-2-[4-(2-methylamino)-piperid-1-yl]-acetamide, N-{2-[2-(4-Amidinophenyl)-ethyl]-1-methyl-benzimidazol-5-yl}-N-methyl-2-[4-(2-tert.butylamino)-piperid-1-yl]-acetamide, N-{2-[2-(4-Amidinophenyl)-ethyl]-1-methyl-benzimidazol-5-yl}-N-methyl-2-[4-(2-bromo-4-chloroamino)-piperid-1-yl]-acetamide, N-{2-[2-(4-Amidinophenyl)-ethyl]-1-methyl-benzimidazol-5-yl}-N-methyl-2-[4-(2-bromo-4-methylamino)-piperid-1-yl]-acetamide, N-{2-[2-(4-Amidinophenyl)-ethyl]-1-methyl-benzimidazol-5-yl}-N-methyl-2-[4-(2-bromo-4-trifluoromethylamino)-piperid-1-yl]-acetamide, N-{2-[2-(4-Amidinophenyl)-ethyl]-1-methyl-benzimidazol-5-yl}-N-methyl-2-[4-(2-bromo-4-isopropylamino)-piperid-1-yl]-acetamide, N-{2-[2-(4-Amidinophenyl)-ethyl]-1-methyl-benzimidazol-5-yl}-N-methyl-2-[4-(2-chloro-4-tert.butylamino)-piperid-1-yl]-acetamide, N-{2-[2-(4-Amidinophenyl)-ethyl]-1-methyl-benzimidazol-5-yl}-N-methyl-2-[4-(2-chloro-N-methylamino)-piperid-1-yl]-acetamide, N-{2-[2-(4-Amidinophenyl)-ethyl]-1-methyl-benzimidazol-5-yl}-N-methyl-2-[4-(2,4-dichloro-N-methylamino)-piperid-1-yl]-acetamide, N-{2-[2-(4-Amidinophenyl)-ethyl]-1-methyl-benzimidazol-5-yl}-N-methyl-2-[4-(4-chlorophenylamino)-piperid-1-yl]-acetamide, N-{2-[2-(4-Amidinophenyl)-ethyl]-1-methyl-benzimidazol-5-yl}-N-methyl-2-[4-(3-chlorophenylamino)-piperid-1-yl]-acetamide, N-{2-[2-(4-Amidinophenyl)-ethyl]-1-methyl-benzimidazol-5-yl}-N-methyl-2-[4-(3,4-dichlorophenylamino)-piperid-1-yl]-acetamide and N-{2-[2-(4-Amidinophenyl)-ethyl]-1-methyl-benzimidazol-5-yl}-N-methyl-2-[4-(phenylamino)-piperid-1-yl]-acetamide, or their tautomers, racemates, enantiomers, diastereomers and mixtures thereof, or the pharmaceutically acceptable acid addition salts thereof.

5. A method of treating an inflammatory disease or condition comprising administering to a patient in need thereof a therapeutically effective amount of a compound according to claim 1.

6. A method of treating an allergic condition or disease comprising administering to a patient in need thereof a therapeutically effective amount of a compound according to claim 1.

7. A method of treating a disease chosen from bronchial asthma, allergic rhinitis, allergic conjunctivitis, atopic dermatitis, urticaria, allergic otitis, allergic gastro-intestinal disorders, Crohn's disease, ulcerative colitis, anaphylactic shock, septic shock, shock lung (ARDS) and arthritis comprising administering to a patient in need thereof a therapeutically effective amount of a compound according to claim 1.

8. A method of treating a disease chosen from fibroses chosen from lung fibrosis, fibrosing alveolitis and scarring, collagenoses chosen from lupus erythematodes and selerodermia, arteriosclerosis, psoriasis and neoplasia comprising administering to a patient in need thereof a therapeutically effective amount of a compound according to claim 1.

9. A pharmaceutical composition comprising a therapeutically effective amount of one or more compounds according to claim 1 and one or more pharmaceutically acceptable carriers and/or adjuvants.

10. A process for preparing compounds of general formula (Ia)

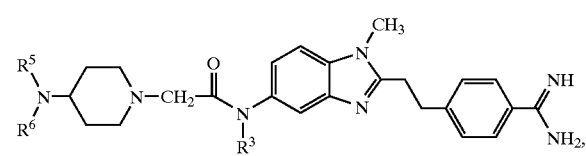

(Ia)

wherein the groups $R^3$, $R^5$ and $R^6$ have the meanings given in claim 1, comprising:
reacting a compound of general formula:

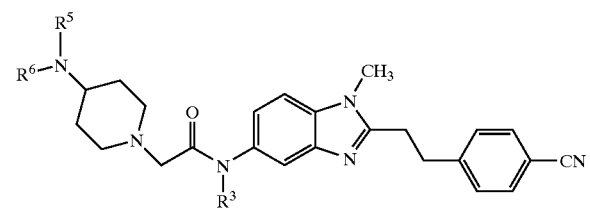

wherein the groups $R^3$, $R^5$ and $R^6$ have the meanings given in claim 1 with:
i) a corresponding alcohol optionally mixed with another organic solvent in the presence of an acid;
ii) a corresponding amide with a trialkyloxonium salt in a suitable solvent at a temperature between −10 and 50° C. and subsequent aminolysis by reacting with an alcoholic ammonia solution;
iii) a sulphur nucleophile optionally in the presence of a base in a suitable solvent at 20-100° C., subsequently reacting with a methylating agent in a suitable solvent at −10 and 50° C. and subsequently reacting with ammonia, ammonium carbonate or ammonium chloride in a suitable alcohol at a temperature between −10 and 50° C.;
iv) lithium hexamethyl disilazide in a suitable organic solvent at a temperature between −20 and 50° C. and subsequent hydrolyzing, or
v) ammonium chloride and trimethylaluminium in a suitable solvent at a temperature between 20 and 150° C.;

and subsequently isolating the product compound of general formula (Ia).

* * * * *